US010717783B2

(12) United States Patent
Gao et al.

(10) Patent No.: US 10,717,783 B2
(45) Date of Patent: Jul. 21, 2020

(54) BISPECIFIC TETRAVALENT ANTIBODIES AND METHODS OF MAKING AND USING THEREOF

(71) Applicant: SystImmune, Inc., Redmond, WA (US)

(72) Inventors: Zeren Gao, Redmond, WA (US); Yi Zhu, Chengdu (CN); Phil Tan, Redmond, WA (US); Blair R. Renshaw, Redmond, WA (US); Brian R. Kovacevich, Redmond, WA (US)

(73) Assignee: Zeren Gao, Redmond, WA (US)

( * ) Notice: Subject to any disclaimer, the term of this patent is extended or adjusted under 35 U.S.C. 154(b) by 0 days.

(21) Appl. No.: 15/538,189

(22) PCT Filed: Dec. 19, 2015

(86) PCT No.: PCT/US2015/066952

§ 371 (c)(1),
(2) Date: Jun. 20, 2017

(87) PCT Pub. No.: WO2016/106158

PCT Pub. Date: Jun. 30, 2016

(65) Prior Publication Data

US 2017/0369587 A1 Dec. 28, 2017

Related U.S. Application Data

(60) Provisional application No. 62/095,348, filed on Dec. 22, 2014.

(51) Int. Cl.

| | |
|---|---|
| ***C07K 16/30*** | (2006.01) |
| ***C07K 16/32*** | (2006.01) |
| ***A61K 47/68*** | (2017.01) |
| ***C07K 16/28*** | (2006.01) |
| ***A61K 39/395*** | (2006.01) |
| ***A61K 45/06*** | (2006.01) |
| ***C07K 16/46*** | (2006.01) |
| *A61K 39/00* | (2006.01) |

(52) U.S. Cl.

CPC ...... *C07K 16/3015* (2013.01); *A61K 39/3955* (2013.01); *A61K 39/39558* (2013.01); *A61K 45/06* (2013.01); *A61K 47/6803* (2017.08); *A61K 47/6849* (2017.08); *A61K 47/6851* (2017.08); *C07K 16/2863* (2013.01); *C07K 16/32* (2013.01); *C07K 16/468* (2013.01); *A61K 2039/505* (2013.01); *A61K 2039/5152* (2013.01); *C07K 2317/21* (2013.01); *C07K 2317/24* (2013.01); *C07K 2317/31* (2013.01); *C07K 2317/35* (2013.01); *C07K 2317/622* (2013.01); *C07K 2317/64* (2013.01); *C07K 2317/73* (2013.01); *C07K 2317/732* (2013.01); *C07K 2317/76* (2013.01); *C07K 2317/92* (2013.01); *C07K 2317/94* (2013.01)

(58) Field of Classification Search

None

See application file for complete search history.

(56) References Cited

U.S. PATENT DOCUMENTS

| | | | | |
|---|---|---|---|---|
| 2003/0153735 A1* | 8/2003 | Breece | C07K 1/22 530/413 |
| 2010/0256338 A1* | 10/2010 | Brinkmann | C07K 16/00 530/387.3 |
| 2014/0056895 A1 | 2/2014 | Baurin et al. | |
| 2014/0135482 A1 | 5/2014 | Bossenmaier et al. | |
| 2014/0170148 A1* | 6/2014 | De Goeij | A61K 47/6879 424/136.1 |

FOREIGN PATENT DOCUMENTS

| | | | | |
|---|---|---|---|---|
| CN | 102250246 A | 11/2011 | |
| CN | 102250247 A | 11/2011 | |
| CN | 103384681 A | 1/2013 | |
| CN | 104144949 B | 6/2013 | |
| CN | 103796678 Y | 5/2014 | |
| WO | WO 2012/143523 * | 10/2012 | C07K 16/32 |
| WO | WO2014144357 A1 | 9/2014 | |

OTHER PUBLICATIONS

Dong et al. (mAbs, 3(3): 273-288, 2011).*
Hoet et al. (Nature Biotechnology, 23(3): 344-349, 2005).*
Chen et al. (Advanced Drug Delivery Reviews, 65: 1357-1369, Oct. 2013).*
Hu et al. "Four-in-One Antibodies Have Superior Cancer Inhibitory Activity against EGFR, HERZ, HER3, and VEGF through Disruption of HER/MET Crosstalk," Cancer Res. Nov. 4, 2014 (Nov. 4, 2014), vol. 79, pp. 159-170.
Shi Hu et, al., Four-in-one Antibodies have Superior cancer Inhibitory activity against EGFR, HER2, HER3, and VEGF through Disruption of HER/MET Cancer Res; 75(1) Jan. 1, 2015, 160-168.

* cited by examiner

*Primary Examiner* — Nelson B Moseley, II
(74) *Attorney, Agent, or Firm* — Zhihua Han; WEN IP LLC

(57) ABSTRACT

A bispecific tetravalent antibody comprising an IgG having a pair of heavy chains and a pair of light chains, and two scFv components being connected to either C or N terminals of the heavy or light chains. The bispecific tetravalent antibody may have a binding specificity for two different epitopes on HER2 receptor.

18 Claims, 12 Drawing Sheets

Specification includes a Sequence Listing.

4X1

4X2

4C1

4C3

4C4

4C5

4C6

4C7

4C8

4C10

4C11

| IC50 (nM) | | | | | |
|---|---|---|---|---|---|
| SI-4C1 | SI-4C2 | SI-4C1 + SI-4C2 | SI-4X1 | SI-4X2 | SI-4X3 |
| 2.63 | 0.51 | 0.48 | 3.28 | N/A | N/A |

SEQUENCE LISTING

```
<160> NUMBER OF SEQ ID NOS: 81

<210> SEQ ID NO 1
<211> LENGTH: 642
<212> TYPE: DNA
<213> ORGANISM: Artificial Sequence
<220> FEATURE:
<223> OTHER INFORMATION: Synthesized

<400> SEQUENCE: 1

gacatccaga tgacacaatc tcctagcagt ctgagcgcaa gtgttggaga tcgtgtcacc      60

atcacatgca aggccagcca ggatgtgagc attggagtcg cctggtatca gcagaaaccc     120

ggcaaggcac ccaagctgct gatctactcg gccagttaca gatacactgg cgtaccttcg     180

aggtttagtg gtagcggttc tggaaccgat ttcaccctca ccattagctc cctccaaccc     240

gaggacttcg ccacctacta ctgccagcaa tactacatct acccttacac gttcggccaa     300

ggcactaagg tcgagattaa acgtacggtg gctgcaccat ctgtcttcat cttcccgcca     360

tctgatgagc agttgaaatc tggaactgcc tctgttgtgt gcctgctgaa taacttctat     420

cccagagagg ccaaagtaca gtggaaggtg gataacgccc tccaatcggg taactcccag     480

gagagtgtca cagagcagga cagcaaggac agcacctaca gcctcagcag caccctgacg     540

ctgagcaaag cagactacga gaaacacaaa gtctacgcct gcgaagtcac ccatcagggc     600

ctgagctcgc ccgtcacaaa gagcttcaac aggggagagt gt                        642


<210> SEQ ID NO 2
<211> LENGTH: 324
<212> TYPE: DNA
<213> ORGANISM: Artificial Sequence
<220> FEATURE:
<223> OTHER INFORMATION: Synthesized

<400> SEQUENCE: 2

gacatccaga tgacacaatc tcctagcagt ctgagcgcaa gtgttggaga tcgtgtcacc      60

atcacatgca aggccagcca ggatgtgagc attggagtcg cctggtatca gcagaaaccc     120

ggcaaggcac ccaagctgct gatctactcg gccagttaca gatacactgg cgtaccttcg     180

aggtttagtg gtagcggttc tggaaccgat ttcaccctca ccattagctc cctccaaccc     240

gaggacttcg ccacctacta ctgccagcaa tactacatct acccttacac gttcggccaa     300
```

```
ggcactaagg tcgagattaa acgt                                         324


<210> SEQ ID NO 3
<211> LENGTH: 214
<212> TYPE: PRT
<213> ORGANISM: Artificial Sequence
<220> FEATURE:
<223> OTHER INFORMATION: Synthesized

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 4
<211> LENGTH: 107
<212> TYPE: PRT
<213> ORGANISM: Artificial Sequence
<220> FEATURE:
<223> OTHER INFORMATION: Synthesized

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

-continued

```
Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105


<210> SEQ ID NO 5
<211> LENGTH: 1347
<212> TYPE: DNA
<213> ORGANISM: Artificial Sequence
<220> FEATURE:
<223> OTHER INFORMATION: Synthesized

<400> SEQUENCE: 5

gaagtgcagc tcgtcgaaag cggtggcgga ctggttcagc ccggtggttc tctgcggctg     60

tcttgtgctg cctcgggttt cacgttcact gactacacaa tggactgggt gcgtcaggct    120

cctggaaagg gattggagtg ggtagccgac gttaatccaa actccggcgg gagcatctac    180

aaccagaggt tcaaggggag gttcactctg agcgtggatc gctccaagaa cacgctgtac    240

ctccagatga actctctcag ggccgaggac acggctgttt actattgcgc gaggaacctg    300

ggtccttcct tctacttcga ctactgggga cagggaaccc tggtgaccgt cagctccgct    360

agcaccaagg gcccatcggt cttccccctg gcaccctcct ccaagagcac ctctgggggc    420

acagcggccc tgggctgcct ggtcaaggac tacttccccg aaccggtgac ggtgtcgtgg    480

aactcaggcg ccctgaccag cggcgtgcac accttcccgg ctgtcctaca gtcctcagga    540

ctctactccc tcagcagcgt ggtgaccgtg ccctccagca gcttgggcac ccagacctac    600

atctgcaacg tgaatcacaa gcccagcaac accaaggtgg acaagagagt tgagcccaaa    660

tcttgtgaca aaactcacac atgcccaccg tgcccagcac ctgaactcct ggggggaccg    720

tcagtcttcc tcttcccccc aaaacccaag gacaccctca tgatctcccg gacccctgag    780

gtcacatgcg tggtggtgga cgtgagccac gaagaccctg aggtcaagtt caactggtac    840

gtggacggcg tggaggtgca taatgccaag acaaagccgc gggaggagca gtacaacagc    900

acgtaccgtg tggtcagcgt cctcaccgtc ctgcaccagg actggctgaa tggcaaggag    960

tacaagtgca aggtctccaa caaagccctc ccagccccca tcgagaaaac catctccaaa   1020

gccaaagggc agccccgaga accacaggtg tacaccctgc ccccatcccg ggaggagatg   1080

accaagaacc aggtcagcct gacctgcctg gtcaaaggct tctatcccag cgacatcgcc   1140

gtggagtggg agagcaatgg gcagccggag aacaactaca agaccacgcc tcccgtgctg   1200

gactccgacg gctccttctt cctctatagc aagctcaccg tggacaagag caggtggcag   1260

caggggaacg tcttctcatg ctccgtgatg catgaggctc tgcacaacca ctacacgcag   1320

aagagcctct ccctgtctcc gggtaaa                                         1347


<210> SEQ ID NO 6
<211> LENGTH: 357
<212> TYPE: DNA
<213> ORGANISM: Artificial Sequence
<220> FEATURE:
<223> OTHER INFORMATION: Synthesized

<400> SEQUENCE: 6

gaagtgcagc tcgtcgaaag cggtggcgga ctggttcagc ccggtggttc tctgcggctg     60

tcttgtgctg cctcgggttt cacgttcact gactacacaa tggactgggt gcgtcaggct    120

cctggaaagg gattggagtg ggtagccgac gttaatccaa actccggcgg gagcatctac    180

aaccagaggt tcaaggggag gttcactctg agcgtggatc gctccaagaa cacgctgtac    240
```

```
ctccagatga actctctcag ggccgaggac acggctgttt actattgcgc gaggaacctg    300

ggtccttcct tctacttcga ctactgggga cagggaaccc tggtgaccgt cagctcc       357


<210> SEQ ID NO 7
<211> LENGTH: 449
<212> TYPE: PRT
<213> ORGANISM: Artificial Sequence
<220> FEATURE:
<223> OTHER INFORMATION: Synthesized

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
```

-continued 340 345 350

Leu Pro Pro Ser Arg Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 8
<211> LENGTH: 119
<212> TYPE: PRT
<213> ORGANISM: Artificial Sequence
<220> FEATURE:
<223> OTHER INFORMATION: Synthesized

<400> SEQUENCE: 8

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Thr Asp Tyr
20 25 30

Thr Met Asp Trp Val Arg Gln Ala Pro Gly Lys Gly Leu Glu Trp Val
35 40 45

Ala Asp Val Asn Pro Asn Ser Gly Gly Ser Ile Tyr Asn Gln Arg Phe
50 55 60

Lys Gly Arg Phe Thr Leu Ser Val Asp Arg Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asn Leu Gly Pro Ser Phe Tyr Phe Asp Tyr Trp Gly Gln Gly
100 105 110

Thr Leu Val Thr Val Ser Ser
115

<210> SEQ ID NO 9
<211> LENGTH: 642
<212> TYPE: DNA
<213> ORGANISM: Artificial Sequence
<220> FEATURE:
<223> OTHER INFORMATION: Synthesized

<400> SEQUENCE: 9
gatatccaga tgacccagtc cccgagctcc ctgtccgcct ctgtgggcga tagggtcacc 60
atcacctgcc gtgccagtca ggatgtgaat actgctgtag cctggtatca acagaaacca 120
ggaaaagctc cgaaactact gatttactcg gcatccttcc tctactctgg agtcccttct 180
cgcttctctg gctccagatc tgggacggat ttcactctga ccatcagcag tctgcagccg 240
gaagacttcg caacttatta ctgtcagcaa cattatacta ctcctcccac gttcggacag 300
ggtaccaagg tggagatcaa acgtacggtg gctgcaccat ctgtcttcat cttcccgcca 360
tctgatgagc agttgaaatc tggaactgcc tctgttgtgt gcctgctgaa taacttctat 420

```
cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642


<210> SEQ ID NO 10
<211> LENGTH: 321
<212> TYPE: DNA
<213> ORGANISM: Artificial Sequence
<220> FEATURE:
<223> OTHER INFORMATION: Synthesized

<400> SEQUENCE: 10

gatatccaga tgacccagtc cccgagctcc ctgtccgcct ctgtgggcga tagggtcacc     60

atcacctgcc gtgccagtca ggatgtgaat actgctgtag cctggtatca acagaaacca    120

ggaaaagctc cgaaactact gatttactcg gcatccttcc tctactctgg agtcccttct    180

cgcttctctg gctccagatc tgggacggat ttcactctga ccatcagcag tctgcagccg    240

gaagacttcg caacttatta ctgtcagcaa cattatacta ctcctcccac gttcggacag    300

ggtaccaagg tggagatcaa a                                              321


<210> SEQ ID NO 11
<211> LENGTH: 214
<212> TYPE: PRT
<213> ORGANISM: Artificial Sequence
<220> FEATURE:
<223> OTHER INFORMATION: Synthesized

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

-continued

```
Phe Asn Arg Gly Glu Cys
    210


<210> SEQ ID NO 12
<211> LENGTH: 107
<212> TYPE: PRT
<213> ORGANISM: Artificial Sequence
<220> FEATURE:
<223> OTHER INFORMATION: Synthesized

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105


<210> SEQ ID NO 13
<211> LENGTH: 1350
<212> TYPE: DNA
<213> ORGANISM: Artificial Sequence
<220> FEATURE:
<223> OTHER INFORMATION: Synthesized

<400> SEQUENCE: 13

gaggttcagc tggtggagtc tggcggtggc ctggtgcagc caggggggctc actccgtttg      60

tcctgtgcag cttctggctt caacattaaa gacacctata tacactgggt gcgtcaggcc     120

ccgggtaagg gcctggaatg ggttgcaagg atttatccta cgaatggtta tactagatat     180

gccgatagcg tcaagggccg tttcactata agcgcagaca catccaaaaa cacagcctac     240

ctgcagatga acagcctgcg tgctgaggac actgccgtct attattgttc tagatgggga     300

ggggacggct tctatgctat ggactactgg ggtcaaggaa ccctggtcac cgtctcctcg     360

gctagcacca agggcccatc ggtcttcccc ctggcaccct cctccaagag cacctctggg     420

ggcacagcgg ccctgggctg cctggtcaag gactacttcc ccgaaccggt gacggtgtcg     480

tggaactcag gcgccctgac cagcggcgtg cacaccttcc cggctgtcct acagtcctca     540

ggactctact ccctcagcag cgtggtgacc gtgccctcca gcagcttggg cacccagacc     600

tacatctgca acgtgaatca caagcccagc aacaccaagg tggacaagag agttgagccc     660

aaatcttgtg acaaaactca cacatgccca ccgtgcccag cacctgaact cctgggggga     720

ccgtcagtct tcctcttccc cccaaaaccc aaggacaccc tcatgatctc ccggacccct     780

gaggtcacat gcgtggtggt ggacgtgagc cacgaagacc ctgaggtcaa gttcaactgg     840

tacgtggacg gcgtggaggt gcataatgcc aagacaaagc cgcgggagga gcagtacaac     900

agcacgtacc gtgtggtcag cgtcctcacc gtcctgcacc aggactggct gaatggcaag     960

gagtacaagt gcaaggtctc caacaaagcc ctcccagccc ccatcgagaa aaccatctcc    1020
```

-continued

```
aaagccaaag ggcagccccg agaaccacag gtgtacaccc tgcccccatc ccgggaggag   1080

atgaccaaga accaggtcag cctgacctgc ctggtcaaag gcttctatcc cagcgacatc   1140

gccgtggagt gggagagcaa tgggcagccg gagaacaact acaagaccac gcctcccgtg   1200

ctggactccg acggctcctt cttcctctat agcaagctca ccgtggacaa gagcaggtgg   1260

cagcagggga acgtcttctc atgctccgtg atgcatgagg ctctgcacaa ccactacacg   1320

cagaagagcc tctccctgtc tccgggtaaa                                    1350
```

<210> SEQ ID NO 14
<211> LENGTH: 360
<212> TYPE: DNA
<213> ORGANISM: Artificial Sequence
<220> FEATURE:
<223> OTHER INFORMATION: Synthesized

<400> SEQUENCE: 14

```
gaggttcagc tggtggagtc tggcggtggc ctggtgcagc caggggggctc actccgtttg     60

tcctgtgcag cttctggctt caacattaaa gacacctata tacactgggt gcgtcaggcc    120

ccgggtaagg gcctggaatg ggttgcaagg atttatccta cgaatggtta tactagatat    180

gccgatagcg tcaagggccg tttcactata agcgcagaca catccaaaaa cacagcctac    240

ctgcagatga acagcctgcg tgctgaggac actgccgtct attattgttc tagatgggga    300

ggggacggct tctatgctat ggactactgg ggtcaaggaa ccctggtcac cgtctcctcg    360
```

<210> SEQ ID NO 15
<211> LENGTH: 450
<212> TYPE: PRT
<213> ORGANISM: Artificial Sequence
<220> FEATURE:
<223> OTHER INFORMATION: Synthesized

<400> SEQUENCE: 15

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

Ser Ser Ser Leu Gly Thr Gln Thr Tyr Ile Cys Asn Val Asn His Lys
195 200 205

Pro Ser Asn Thr Lys Val Asp Lys Arg Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Glu Glu Met Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly Lys
450

<210> SEQ ID NO 16
<211> LENGTH: 120
<212> TYPE: PRT
<213> ORGANISM: Artificial Sequence
<220> FEATURE:
<223> OTHER INFORMATION: Synthesized

<400> SEQUENCE: 16

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

-continued

```
Ser Arg Trp Gly Gly Asp Gly Phe Tyr Ala Met Asp Tyr Trp Gly Gln
            100                 105                 110

Gly Thr Leu Val Thr Val Ser Ser
        115                 120


<210> SEQ ID NO 17
<211> LENGTH: 1450
<212> TYPE: DNA
<213> ORGANISM: Artificial Sequence
<220> FEATURE:
<223> OTHER INFORMATION: Synthesized

<400> SEQUENCE: 17

gagcccaaat cttgtgacaa aactcacaca tgcccaccgt gcccagcacc tgaactcctg      60

gggggaccgt cagtcttcct cttcccccca aaacccaagg acaccctcat gatctcccgg     120

acccctgagg tcacatgcgt ggtggtggac gtgagccacg aagaccctga ggtcaagttc     180

aactggtacg tggacggcgt ggaggtgcat aatgccaaga caaagccgcg ggaggagcag     240

tacaacagca cgtaccgtgt ggtcagcgtc ctcaccgtcc tgcaccagga ctggctgaat     300

ggcaaggagt acaagtgcaa ggtctccaac aaagccctcc cagcccccat cgagaaaacc     360

atctccaaag ccaaagggca gccccgagaa ccacaggtgt acaccctgcc cccatcccgg     420

gaggagatga ccaagaacca ggtcagcctg acctgcctgg tcaaaggctt ctatcccagc     480

gacatcgccg tggagtggga gagcaatggg cagccggaga acaactacaa gaccacgcct     540

cccgtgctgg actccgacgg ctccttcttc ctctatagca agctcaccgt ggacaagagc     600

aggtggcagc aggggaacgt cttctcatgc tccgtgatgc atgaggctct gcacaaccac     660

tacacgcaga agagcctctc cctgtctccg ggtaaaggcg gtggaggatc cggcggtggt     720

ggatcagaag tgcagctcgt cgaaagcggt ggcggactgg ttcagcccgg tggttctctg     780

cggctgtctt gtgctgcctc gggtttcacg ttcactgact acacaatgga ctgggtgcgt     840

caggctcctg gaaagggatt ggagtgggta gccgacgtta atccaaactc cggcgggagc     900

atctacaacc agaggttcaa ggggaggttc actctgagcg tggatcgctc caagaacacg     960

ctgtacctcc agatgaactc tctcagggcc gaggacacgg ctgtttacta ttgcgcgagg    1020

aacctgggtc cttccttcta cttcgactac tggggacagg gaaccctggt gaccgtcagc    1080

tccggtggag gcggttcagg cggaggtggt tccggcggtg gcggctccga catccagatg    1140

acacaatctc ctagcagtct gagcgcaagt gttggagatc gtgtcaccat cacatgcaag    1200

gccagccagg atgtgagcat tggagtcgcc tggtatcagc agaaacccgg caaggcaccc    1260

aagctgctga tctactcggc cagttacaga tacactggcg taccttcgag gtttagtggt    1320

agcggttctg gaaccgattt caccctcacc attagctccc tccaacccga ggacttcgcc    1380

acctactact gccagcaata ctacatctac ccttacacgt tcggccaagg cactaaggtc    1440

gagattaaat                                                           1450


<210> SEQ ID NO 18
<211> LENGTH: 483
<212> TYPE: PRT
<213> ORGANISM: Artificial Sequence
<220> FEATURE:
<223> OTHER INFORMATION: Synthesized

<400> SEQUENCE: 18

Glu Pro Lys Ser Cys Asp Lys Thr His Thr Cys Pro Pro Cys Pro Ala
1               5                   10                  15
```

-continued

```
Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Gly Gly Gly Gly Ser Gly Gly Gly
225                 230                 235                 240

Gly Ser Glu Val Gln Leu Val Glu Ser Gly Gly Gly Leu Val Gln Pro
                245                 250                 255

Gly Gly Ser Leu Arg Leu Ser Cys Ala Ala Ser Gly Phe Thr Phe Thr
            260                 265                 270

Asp Tyr Thr Met Asp Trp Val Arg Gln Ala Pro Gly Lys Gly Leu Glu
        275                 280                 285

Trp Val Ala Asp Val Asn Pro Asn Ser Gly Gly Ser Ile Tyr Asn Gln
    290                 295                 300

Arg Phe Lys Gly Arg Phe Thr Leu Ser Val Asp Arg Ser Lys Asn Thr
305                 310                 315                 320

Leu Tyr Leu Gln Met Asn Ser Leu Arg Ala Glu Asp Thr Ala Val Tyr
                325                 330                 335

Tyr Cys Ala Arg Asn Leu Gly Pro Ser Phe Tyr Phe Asp Tyr Trp Gly
            340                 345                 350

Gln Gly Thr Leu Val Thr Val Ser Ser Gly Gly Gly Gly Ser Gly Gly
        355                 360                 365

Gly Gly Ser Gly Gly Gly Gly Ser Asp Ile Gln Met Thr Gln Ser Pro
    370                 375                 380

Ser Ser Leu Ser Ala Ser Val Gly Asp Arg Val Thr Ile Thr Cys Lys
385                 390                 395                 400

Ala Ser Gln Asp Val Ser Ile Gly Val Ala Trp Tyr Gln Gln Lys Pro
                405                 410                 415

Gly Lys Ala Pro Lys Leu Leu Ile Tyr Ser Ala Ser Tyr Arg Tyr Thr
            420                 425                 430
```

-continued

Gly Val Pro Ser Arg Phe Ser Gly Ser Gly Ser Gly Thr Asp Phe Thr
        435                 440                 445

Leu Thr Ile Ser Ser Leu Gln Pro Glu Asp Phe Ala Thr Tyr Tyr Cys
    450                 455                 460

Gln Gln Tyr Tyr Ile Tyr Pro Tyr Thr Phe Gly Gln Gly Thr Lys Val
465                 470                 475                 480

Glu Ile Lys

<210> SEQ ID NO 19
<211> LENGTH: 241
<212> TYPE: PRT
<213> ORGANISM: Artificial Sequence
<220> FEATURE:
<223> OTHER INFORMATION: Synthesized

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Lys Ala Ser
145                 150                 155                 160

Gln Asp Val Ser Ile Gly Val Ala Trp Tyr Gln Gln Lys Pro Gly Lys
                165                 170                 175

Ala Pro Lys Leu Leu Ile Tyr Ser Ala Ser Tyr Arg Tyr Thr Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Tyr Tyr Ile Tyr Pro Tyr Thr Phe Gly Gln Gly Thr Lys Val Glu Ile
225                 230                 235                 240

Lys

<210> SEQ ID NO 20
<211> LENGTH: 1452
<212> TYPE: DNA
<213> ORGANISM: Artificial Sequence
<220> FEATURE:
<223> OTHER INFORMATION: Synthesized

<400> SEQUENCE: 20
gagcccaaat cttgtgacaa aactcacaca tgcccaccgt gcccagcacc tgaactcctg     60

```
gggggaccgt cagtcttcct cttcccccca aaacccaagg acaccctcat gatctcccgg    120

acccctgagg tcacatgcgt ggtggtggac gtgagccacg aagaccctga ggtcaagttc    180

aactggtacg tggacggcgt ggaggtgcat aatgccaaga caaagccgcg ggaggagcag    240

tacaacagca cgtaccgtgt ggtcagcgtc ctcaccgtcc tgcaccagga ctggctgaat    300

ggcaaggagt acaagtgcaa ggtctccaac aaagccctcc cagcccccat cgagaaaacc    360

atctccaaag ccaaagggca gccccgagaa ccacaggtgt acaccctgcc cccatcccgg    420

gaggagatga ccaagaacca ggtcagcctg acctgcctgg tcaaaggctt ctatcccagc    480

gacatcgccg tggagtggga gagcaatggg cagccggaga acaactacaa gaccacgcct    540

cccgtgctgg actccgacgg ctccttcttc ctctatagca agctcaccgt ggacaagagc    600

aggtggcagc aggggaacgt cttctcatgc tccgtgatgc atgaggctct gcacaaccac    660

tacacgcaga agagcctctc cctgtctccg ggtaaaggcg gtggaggatc cggcggtggt    720

ggatcagagg ttcagctggt ggagtctggc ggtggcctgg tgcagccagg gggctcactc    780

cgtttgtcct gtgcagcttc tggcttcaac attaaagaca cctatataca ctgggtgcgt    840

caggccccgg gtaagggcct ggaatgggtt gcaaggattt atcctacgaa tggttatact    900

agatatgccg atagcgtcaa gggccgtttc actataagcg cagacacatc caaaaacaca    960

gcctacctgc agatgaacag cctgcgtgct gaggacactg ccgtctatta ttgttctaga   1020

tggggagggg acggcttcta tgctatggac tactggggtc aaggaaccct ggtcaccgtc   1080

tcctcgggtg gaggcggttc aggcggaggt ggttccggcg gtggcggctc cgatatccag   1140

atgacccagt ccccgagctc cctgtccgcc tctgtgggcg atagggtcac catcacctgc   1200

cgtgccagtc aggatgtgaa tactgctgta gcctggtatc aacagaaacc aggaaaagct   1260

ccgaaactac tgatttactc ggcatccttc ctctactctg gagtcccttc tcgcttctct   1320

ggctccagat ctgggacgga tttcactctg accatcagca gtctgcagcc ggaagacttc   1380

gcaacttatt actgtcagca acattatact actcctccca cgttcggaca gggtaccaag   1440

gtggagatca aa                                                        1452
```

```
<210> SEQ ID NO 21
<211> LENGTH: 484
<212> TYPE: PRT
<213> ORGANISM: Artificial Sequence
<220> FEATURE:
<223> OTHER INFORMATION: Synthesized

<400> SEQUENCE: 21

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110
```

```
Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Gly Gly Gly Gly Ser Gly Gly Gly
225                 230                 235                 240

Gly Ser Glu Val Gln Leu Val Glu Ser Gly Gly Gly Leu Val Gln Pro
                245                 250                 255

Gly Gly Ser Leu Arg Leu Ser Cys Ala Ala Ser Gly Phe Asn Ile Lys
            260                 265                 270

Asp Thr Tyr Ile His Trp Val Arg Gln Ala Pro Gly Lys Gly Leu Glu
        275                 280                 285

Trp Val Ala Arg Ile Tyr Pro Thr Asn Gly Tyr Thr Arg Tyr Ala Asp
    290                 295                 300

Ser Val Lys Gly Arg Phe Thr Ile Ser Ala Asp Thr Ser Lys Asn Thr
305                 310                 315                 320

Ala Tyr Leu Gln Met Asn Ser Leu Arg Ala Glu Asp Thr Ala Val Tyr
                325                 330                 335

Tyr Cys Ser Arg Trp Gly Gly Asp Gly Phe Tyr Ala Met Asp Tyr Trp
            340                 345                 350

Gly Gln Gly Thr Leu Val Thr Val Ser Ser Gly Gly Gly Gly Ser Gly
        355                 360                 365

Gly Gly Gly Ser Gly Gly Gly Gly Ser Asp Ile Gln Met Thr Gln Ser
    370                 375                 380

Pro Ser Ser Leu Ser Ala Ser Val Gly Asp Arg Val Thr Ile Thr Cys
385                 390                 395                 400

Arg Ala Ser Gln Asp Val Asn Thr Ala Val Ala Trp Tyr Gln Gln Lys
                405                 410                 415

Pro Gly Lys Ala Pro Lys Leu Leu Ile Tyr Ser Ala Ser Phe Leu Tyr
            420                 425                 430

Ser Gly Val Pro Ser Arg Phe Ser Gly Ser Arg Ser Gly Thr Asp Phe
        435                 440                 445

Thr Leu Thr Ile Ser Ser Leu Gln Pro Glu Asp Phe Ala Thr Tyr Tyr
    450                 455                 460

Cys Gln Gln His Tyr Thr Thr Pro Pro Thr Phe Gly Gln Gly Thr Lys
465                 470                 475                 480

Val Glu Ile Lys
```

<210> SEQ ID NO 22
<211> LENGTH: 242
<212> TYPE: PRT
<213> ORGANISM: Artificial Sequence
<220> FEATURE:
<223> OTHER INFORMATION: Synthesized

<400> SEQUENCE: 22

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln His Tyr Thr Thr Pro Pro Thr Phe Gly Gln Gly Thr Lys Val Glu
225                 230                 235                 240

Ile Lys
```

<210> SEQ ID NO 23
<211> LENGTH: 642
<212> TYPE: DNA
<213> ORGANISM: Artificial Sequence
<220> FEATURE:
<223> OTHER INFORMATION: Synthesized

<400> SEQUENCE: 23

```
gacatccaga tgacacaatc tcctagcagt ctgagcgcaa gtgttggaga tcgtgtcacc     60

atcacatgca aggccagcca ggatgtgagc attggagtcg cctggtatca gcagaaaccc    120

ggcaaggcac ccaagctgct gatctactcg gccagttaca gatacactgg cgtaccttcg    180

aggtttagtg gtagcggttc tggaaccgat ttcaccctca ccattagctc cctccaaccc    240

gaggacttcg ccacctacta ctgccagcaa tactacatct acccttacac gttcggccaa    300

ggcactaagg tcgagattaa acgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600
```

-continued

```
ctgagctcgc ccgtcacaaa gagcttcaac aggggagagt gt                    642


<210> SEQ ID NO 24
<211> LENGTH: 324
<212> TYPE: DNA
<213> ORGANISM: Artificial Sequence
<220> FEATURE:
<223> OTHER INFORMATION: Synthesized

<400> SEQUENCE: 24

gacatccaga tgacacaatc tcctagcagt ctgagcgcaa gtgttggaga tcgtgtcacc     60

atcacatgca aggccagcca ggatgtgagc attggagtcg cctggtatca gcagaaaccc    120

ggcaaggcac ccaagctgct gatctactcg gccagttaca gatacactgg cgtaccttcg    180

aggtttagtg gtagcggttc tggaaccgat ttcaccctca ccattagctc cctccaaccc    240

gaggacttcg ccacctacta ctgccagcaa tactacatct acccttacac gttcggccaa    300

ggcactaagg tcgagattaa acgt                                           324


<210> SEQ ID NO 25
<211> LENGTH: 214
<212> TYPE: PRT
<213> ORGANISM: Artificial Sequence
<220> FEATURE:
<223> OTHER INFORMATION: Synthesized

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 26
```

<211> LENGTH: 107
<212> TYPE: PRT
<213> ORGANISM: Artificial Sequence
<220> FEATURE:
<223> OTHER INFORMATION: Synthesized

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 27
<211> LENGTH: 2103
<212> TYPE: DNA
<213> ORGANISM: Artificial Sequence
<220> FEATURE:
<223> OTHER INFORMATION: Synthesized

<400> SEQUENCE: 27
gaagtgcagc tcgtcgaaag cggtggcgga ctggttcagc ccggtggttc tctgcggctg 60
tcttgtgctg cctcgggttt cacgttcact gactacacaa tggactgggt gcgtcaggct 120
cctggaaagg gattggagtg ggtagccgac gttaatccaa actccggcgg gagcatctac 180
aaccagaggt tcaaggggag gttcactctg agcgtggatc gctccaagaa cacgctgtac 240
ctccagatga actctctcag ggccgaggac acggctgttt actattgcgc gaggaacctg 300
ggtccttcct tctacttcga ctactgggga cagggaaccc tggtgaccgt cagctccgct 360
agcaccaagg gcccatcggt cttccccctg gcaccctcct ccaagagcac ctctgggggc 420
acagcggccc tgggctgcct ggtcaaggac tacttccccg aaccggtgac ggtgtcgtgg 480
aactcaggcg ccctgaccag cggcgtgcac accttcccgg ctgtcctaca gtcctcagga 540
ctctactccc tcagcagcgt ggtgaccgtg ccctccagca gcttgggcac ccagacctac 600
atctgcaacg tgaatcacaa gcccagcaac accaaggtgg acaagagagt tgagcccaaa 660
tcttgtgaca aaactcacac atgcccaccg tgcccagcac ctgaactcct ggggggaccg 720
tcagtcttcc tcttcccccc aaaacccaag gacaccctca tgatctcccg gacccctgag 780
gtcacatgcg tggtggtgga cgtgagccac gaagaccctg aggtcaagtt caactggtac 840
gtggacggcg tggaggtgca taatgccaag acaaagccgc gggaggagca gtacaacagc 900
acgtaccgtg tggtcagcgt cctcaccgtc ctgcaccagg actggctgaa tggcaaggag 960
tacaagtgca aggtctccaa caaagccctc ccagccccca tcgagaaaac catctccaaa 1020
gccaaagggc agccccgaga accacaggtg tacaccctgc ccccatcccg ggaggagatg 1080
accaagaacc aggtcagcct gacctgcctg gtcaaaggct tctatcccag cgacatcgcc 1140
gtggagtggg agagcaatgg gcagccggag aacaactaca agaccacgcc tcccgtgctg 1200

-continued gactccgacg gctccttctt cctctatagc aagctcaccg tggacaagag caggtggcag 1260
caggggaacg tcttctcatg ctccgtgatg catgaggctc tgcacaacca ctacacgcag 1320
aagagcctct ccctgtctcc gggtaaaggc ggtggaggat ccggcggtgg tggatcagag 1380
gttcagctgg tggagtctgg cggtggcctg gtgcagccag ggggctcact ccgtttgtcc 1440
tgtgcagctt ctggcttcaa cattaaagac acctatatac actgggtgcg tcaggccccg 1500
ggtaagggcc tggaatgggt tgcaaggatt tatcctacga atggttatac tagatatgcc 1560
gatagcgtca agggccgttt cactataagc gcagacacat ccaaaaacac agcctacctg 1620
cagatgaaca gcctgcgtgc tgaggacact gccgtctatt attgttctag atggggaggg 1680
gacggcttct atgctatgga ctactggggt caaggaaccc tggtcaccgt ctcctcgggt 1740
ggaggcggtt caggcggagg tggttccggc ggtggcggct ccgatatcca gatgacccag 1800
tccccgagct ccctgtccgc ctctgtgggc gatagggtca ccatcacctg ccgtgccagt 1860
caggatgtga atactgctgt agcctggtat caacagaaac caggaaaagc tccgaaacta 1920
ctgatttact cggcatcctt cctctactct ggagtccctt ctcgcttctc tggctccaga 1980
tctgggacgg atttcactct gaccatcagc agtctgcagc cggaagactt cgcaacttat 2040
tactgtcagc aacattatac tactcctccc acgttcggac agggtaccaa ggtggagatc 2100
aaa 2103

<210> SEQ ID NO 28
<211> LENGTH: 357
<212> TYPE: DNA
<213> ORGANISM: Artificial Sequence
<220> FEATURE:
<223> OTHER INFORMATION: Synthesized

<400> SEQUENCE: 28
gaagtgcagc tcgtcgaaag cggtggcgga ctggttcagc ccggtggttc tctgcggctg 60
tcttgtgctg cctcgggttt cacgttcact gactacacaa tggactgggt gcgtcaggct 120
cctggaaagg gattggagtg ggtagccgac gttaatccaa actccggcgg gagcatctac 180
aaccagaggt tcaaggggag gttcactctg agcgtggatc gctccaagaa cacgctgtac 240
ctccagatga actctctcag ggccgaggac acggctgttt actattgcgc gaggaacctg 300
ggtccttcct tctacttcga ctactgggga cagggaaccc tggtgaccgt cagctcc 357

<210> SEQ ID NO 29
<211> LENGTH: 726
<212> TYPE: DNA
<213> ORGANISM: Artificial Sequence
<220> FEATURE:
<223> OTHER INFORMATION: Synthesized

<400> SEQUENCE: 29
gaggttcagc tggtggagtc tggcggtggc ctggtgcagc cagggggctc actccgtttg 60
tcctgtgcag cttctggctt caacattaaa gacacctata tacactgggt gcgtcaggcc 120
ccgggtaagg gcctggaatg ggttgcaagg atttatccta cgaatggtta tactagatat 180
gccgatagcg tcaagggccg tttcactata agcgcagaca catccaaaaa cacagcctac 240
ctgcagatga acagcctgcg tgctgaggac actgccgtct attattgttc tagatgggga 300
ggggacggct tctatgctat ggactactgg ggtcaaggaa ccctggtcac cgtctcctcg 360
ggtggaggcg gttcaggcgg aggtggttcc ggcggtggcg gctccgatat ccagatgacc 420
cagtccccga gctccctgtc cgcctctgtg ggcgataggg tcaccatcac ctgccgtgcc 480

```
agtcaggatg tgaatactgc tgtagcctgg tatcaacaga aaccaggaaa agctccgaaa    540

ctactgattt actcggcatc cttcctctac tctggagtcc cttctcgctt ctctggctcc    600

agatctggga cggatttcac tctgaccatc agcagtctgc agccggaaga cttcgcaact    660

tattactgtc agcaacatta tactactcct cccacgttcg gacagggtac caaggtggag    720

atcaaa                                                               726


<210> SEQ ID NO 30
<211> LENGTH: 701
<212> TYPE: PRT
<213> ORGANISM: Artificial Sequence
<220> FEATURE:
<223> OTHER INFORMATION: Synthesized

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
```

-continued

```
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Gly Gly Gly Ser Gly Gly Gly Gly Ser Glu Val Gln Leu Val
    450                 455                 460

Glu Ser Gly Gly Gly Leu Val Gln Pro Gly Gly Ser Leu Arg Leu Ser
465                 470                 475                 480

Cys Ala Ala Ser Gly Phe Asn Ile Lys Asp Thr Tyr Ile His Trp Val
                485                 490                 495

Arg Gln Ala Pro Gly Lys Gly Leu Glu Trp Val Ala Arg Ile Tyr Pro
            500                 505                 510

Thr Asn Gly Tyr Thr Arg Tyr Ala Asp Ser Val Lys Gly Arg Phe Thr
        515                 520                 525

Ile Ser Ala Asp Thr Ser Lys Asn Thr Ala Tyr Leu Gln Met Asn Ser
    530                 535                 540

Leu Arg Ala Glu Asp Thr Ala Val Tyr Tyr Cys Ser Arg Trp Gly Gly
545                 550                 555                 560

Asp Gly Phe Tyr Ala Met Asp Tyr Trp Gly Gln Gly Thr Leu Val Thr
                565                 570                 575

Val Ser Ser Gly Gly Gly Gly Ser Gly Gly Gly Gly Ser Gly Gly Gly
            580                 585                 590

Gly Ser Asp Ile Gln Met Thr Gln Ser Pro Ser Ser Leu Ser Ala Ser
        595                 600                 605

Val Gly Asp Arg Val Thr Ile Thr Cys Arg Ala Ser Gln Asp Val Asn
    610                 615                 620

Thr Ala Val Ala Trp Tyr Gln Gln Lys Pro Gly Lys Ala Pro Lys Leu
625                 630                 635                 640

Leu Ile Tyr Ser Ala Ser Phe Leu Tyr Ser Gly Val Pro Ser Arg Phe
                645                 650                 655

Ser Gly Ser Arg Ser Gly Thr Asp Phe Thr Leu Thr Ile Ser Ser Leu
            660                 665                 670

Gln Pro Glu Asp Phe Ala Thr Tyr Tyr Cys Gln Gln His Tyr Thr Thr
        675                 680                 685

Pro Pro Thr Phe Gly Gln Gly Thr Lys Val Glu Ile Lys
    690                 695                 700
```

<210> SEQ ID NO 31
<211> LENGTH: 119
<212> TYPE: PRT
<213> ORGANISM: Artificial Sequence
<220> FEATURE:
<223> OTHER INFORMATION: Synthesized

<400> SEQUENCE: 31

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Thr Asp Tyr
20 25 30

Thr Met Asp Trp Val Arg Gln Ala Pro Gly Lys Gly Leu Glu Trp Val
35 40 45

Ala Asp Val Asn Pro Asn Ser Gly Gly Ser Ile Tyr Asn Gln Arg Phe
50 55 60

Lys Gly Arg Phe Thr Leu Ser Val Asp Arg Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asn Leu Gly Pro Ser Phe Tyr Phe Asp Tyr Trp Gly Gln Gly
100 105 110

Thr Leu Val Thr Val Ser Ser
115

<210> SEQ ID NO 32
<211> LENGTH: 242
<212> TYPE: PRT
<213> ORGANISM: Artificial Sequence
<220> FEATURE:
<223> OTHER INFORMATION: Synthesized

<400> SEQUENCE: 32

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Asp Ile Gln Met Thr Gln Ser Pro Ser
130 135 140

Ser Leu Ser Ala Ser Val Gly Asp Arg Val Thr Ile Thr Cys Arg Ala
145 150 155 160

Ser Gln Asp Val Asn Thr Ala Val Ala Trp Tyr Gln Gln Lys Pro Gly
165 170 175

Lys Ala Pro Lys Leu Leu Ile Tyr Ser Ala Ser Phe Leu Tyr Ser Gly
180 185 190

Val Pro Ser Arg Phe Ser Gly Ser Arg Ser Gly Thr Asp Phe Thr Leu
195 200 205

Thr Ile Ser Ser Leu Gln Pro Glu Asp Phe Ala Thr Tyr Tyr Cys Gln

```
    210                 215                 220

Gln His Tyr Thr Thr Pro Pro Thr Phe Gly Gln Gly Thr Lys Val Glu
225                 230                 235                 240

Ile Lys


<210> SEQ ID NO 33
<211> LENGTH: 642
<212> TYPE: DNA
<213> ORGANISM: Artificial Sequence
<220> FEATURE:
<223> OTHER INFORMATION: Synthesized

<400> SEQUENCE: 33

gatatccaga tgacccagtc cccgagctcc ctgtccgcct ctgtgggcga tagggtcacc      60

atcacctgcc gtgccagtca ggatgtgaat actgctgtag cctggtatca acagaaacca     120

ggaaaagctc cgaaactact gatttactcg gcatccttcc tctactctgg agtcccttct     180

cgcttctctg gctccagatc tgggacggat ttcactctga ccatcagcag tctgcagccg     240

gaagacttcg caacttatta ctgtcagcaa cattatacta ctcctcccac gttcggacag     300

ggtaccaagg tggagatcaa acgtacggtg gctgcaccat ctgtcttcat cttcccgcca     360

tctgatgagc agttgaaatc tggaactgcc tctgttgtgt gcctgctgaa taacttctat     420

cccagagagg ccaaagtaca gtggaaggtg gataacgccc tccaatcggg taactcccag     480

gagagtgtca cagagcagga cagcaaggac agcacctaca gcctcagcag caccctgacg     540

ctgagcaaag cagactacga gaaacacaaa gtctacgcct gcgaagtcac ccatcagggc     600

ctgagctcgc ccgtcacaaa gagcttcaac aggggagagt gt                        642


<210> SEQ ID NO 34
<211> LENGTH: 321
<212> TYPE: DNA
<213> ORGANISM: Artificial Sequence
<220> FEATURE:
<223> OTHER INFORMATION: Synthesized

<400> SEQUENCE: 34

gatatccaga tgacccagtc cccgagctcc ctgtccgcct ctgtgggcga tagggtcacc      60

atcacctgcc gtgccagtca ggatgtgaat actgctgtag cctggtatca acagaaacca     120

ggaaaagctc cgaaactact gatttactcg gcatccttcc tctactctgg agtcccttct     180

cgcttctctg gctccagatc tgggacggat ttcactctga ccatcagcag tctgcagccg     240

gaagacttcg caacttatta ctgtcagcaa cattatacta ctcctcccac gttcggacag     300

ggtaccaagg tggagatcaa a                                               321


<210> SEQ ID NO 35
<211> LENGTH: 214
<212> TYPE: PRT
<213> ORGANISM: Artificial Sequence
<220> FEATURE:
<223> OTHER INFORMATION: Synthesized

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45
```

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 36
<211> LENGTH: 107
<212> TYPE: PRT
<213> ORGANISM: Artificial Sequence
<220> FEATURE:
<223> OTHER INFORMATION: Synthesized

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 37
<211> LENGTH: 2103
<212> TYPE: DNA
<213> ORGANISM: Artificial Sequence
<220> FEATURE:
<223> OTHER INFORMATION: Synthesized

<400> SEQUENCE: 37
gaggttcagc tggtggagtc tggcggtggc ctggtgcagc caggggggctc actccgtttg      60 tcctgtgcag cttctggctt caacattaaa gacacctata tacactgggt gcgtcaggcc     120

-continued

```
ccgggtaagg gcctggaatg ggttgcaagg atttatccta cgaatggtta tactagatat    180
gccgatagcg tcaagggccg tttcactata agcgcagaca catccaaaaa cacagcctac    240
ctgcagatga acagcctgcg tgctgaggac actgccgtct attattgttc tagatgggga    300
ggggacggct tctatgctat ggactactgg ggtcaaggaa ccctggtcac cgtctcctcg    360
gctagcacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagag agttgagccc    660
aaatcttgtg acaaaactca cacatgccca ccgtgcccag cacctgaact cctgggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag ggcagccccg agaaccacag gtgtacaccc tgcccccatc ccgggaggag   1080
atgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctat agcaagctca ccgtggacaa gagcaggtgg   1260
cagcagggga acgtcttctc atgctccgtg atgcatgagg ctctgcacaa ccactacacg   1320
cagaagagcc tctccctgtc tccgggtaaa ggcggtggag gatccggcgg tggtggatca   1380
gaagtgcagc tcgtcgaaag cggtggcgga ctggttcagc ccggtggttc tctgcggctg   1440
tcttgtgctg cctcgggttt cacgttcact gactacacaa tggactgggt gcgtcaggct   1500
cctggaaagg gattggagtg ggtagccgac gttaatccaa actccggcgg gagcatctac   1560
aaccagaggt tcaaggggag gttcactctg agcgtggatc gctccaagaa cacgctgtac   1620
ctccagatga actctctcag ggccgaggac acggctgttt actattgcgc gaggaacctg   1680
ggtccttcct tctacttcga ctactgggga cagggaaccc tggtgaccgt cagctccggt   1740
ggaggcggtt caggcggagg tggttccggc ggtggcggct ccgacatcca gatgacacaa   1800
tctcctagca gtctgagcgc aagtgttgga gatcgtgtca ccatcacatg caaggccagc   1860
caggatgtga gcattggagt cgcctggtat cagcagaaac ccggcaaggc acccaagctg   1920
ctgatctact cggccagtta cagatacact ggcgtacctt cgaggtttag tggtagcggt   1980
tctggaaccg atttcaccct caccattagc tccctccaac ccgaggactt cgccacctac   2040
tactgccagc aatactacat ctacccttac acgttcggcc aaggcactaa ggtcgagatt   2100
aaa                                                                 2103
```

<210> SEQ ID NO 38
<211> LENGTH: 360
<212> TYPE: DNA
<213> ORGANISM: Artificial Sequence
<220> FEATURE:
<223> OTHER INFORMATION: Synthesized

<400> SEQUENCE: 38

```
gaggttcagc tggtggagtc tggcggtggc ctggtgcagc caggggggctc actccgtttg     60
```

```
tcctgtgcag cttctggctt caacattaaa gacacctata tacactgggt gcgtcaggcc    120

ccgggtaagg gcctggaatg ggttgcaagg atttatccta cgaatggtta tactagatat    180

gccgatagcg tcaagggccg tttcactata agcgcagaca catccaaaaa cacagcctac    240

ctgcagatga acagcctgcg tgctgaggac actgccgtct attattgttc tagatgggga    300

ggggacggct tctatgctat ggactactgg ggtcaaggaa ccctggtcac cgtctcctcg    360


<210> SEQ ID NO 39
<211> LENGTH: 723
<212> TYPE: DNA
<213> ORGANISM: Artificial Sequence
<220> FEATURE:
<223> OTHER INFORMATION: Synthesized

<400> SEQUENCE: 39

gaagtgcagc tcgtcgaaag cggtggcgga ctggttcagc ccggtggttc tctgcggctg     60

tcttgtgctg cctcgggttt cacgttcact gactacacaa tggactgggt gcgtcaggct    120

cctggaaagg gattggagtg ggtagccgac gttaatccaa actccggcgg gagcatctac    180

aaccagaggt tcaaggggag gttcactctg agcgtggatc gctccaagaa cacgctgtac    240

ctccagatga actctctcag ggccgaggac acggctgttt actattgcgc gaggaacctg    300

ggtccttcct tctacttcga ctactgggga cagggaaccc tggtgaccgt cagctccggt    360

ggaggcggtt caggcggagg tggttccggc ggtggcggct ccgacatcca gatgacacaa    420

tctcctagca gtctgagcgc aagtgttgga gatcgtgtca ccatcacatg caaggccagc    480

caggatgtga gcattggagt cgcctggtat cagcagaaac ccggcaaggc acccaagctg    540

ctgatctact cggccagtta cagatacact ggcgtacctt cgaggtttag tggtagcggt    600

tctggaaccg atttcaccct caccattagc tccctccaac ccgaggactt cgccacctac    660

tactgccagc aatactacat ctacccttac acgttcggcc aaggcactaa ggtcgagatt    720

aaa                                                                  723


<210> SEQ ID NO 40
<211> LENGTH: 701
<212> TYPE: PRT
<213> ORGANISM: Artificial Sequence
<220> FEATURE:
<223> OTHER INFORMATION: Synthesized

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
```

```
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Gly Gly Gly Gly Ser Gly Gly Gly Gly Ser Glu Val Gln Leu
    450                 455                 460

Val Glu Ser Gly Gly Gly Leu Val Gln Pro Gly Gly Ser Leu Arg Leu
465                 470                 475                 480

Ser Cys Ala Ala Ser Gly Phe Thr Phe Thr Asp Tyr Thr Met Asp Trp
                485                 490                 495

Val Arg Gln Ala Pro Gly Lys Gly Leu Glu Trp Val Ala Asp Val Asn
            500                 505                 510

Pro Asn Ser Gly Gly Ser Ile Tyr Asn Gln Arg Phe Lys Gly Arg Phe
        515                 520                 525

Thr Leu Ser Val Asp Arg Ser Lys Asn Thr Leu Tyr Leu Gln Met Asn
    530                 535                 540
```

-continued

```
Ser Leu Arg Ala Glu Asp Thr Ala Val Tyr Tyr Cys Ala Arg Asn Leu
545                 550                 555                 560

Gly Pro Ser Phe Tyr Phe Asp Tyr Trp Gly Gln Gly Thr Leu Val Thr
                565                 570                 575

Val Ser Ser Gly Gly Gly Gly Ser Gly Gly Gly Gly Ser Gly Gly Gly
            580                 585                 590

Gly Ser Asp Ile Gln Met Thr Gln Ser Pro Ser Ser Leu Ser Ala Ser
        595                 600                 605

Val Gly Asp Arg Val Thr Ile Thr Cys Lys Ala Ser Gln Asp Val Ser
    610                 615                 620

Ile Gly Val Ala Trp Tyr Gln Gln Lys Pro Gly Lys Ala Pro Lys Leu
625                 630                 635                 640

Leu Ile Tyr Ser Ala Ser Tyr Arg Tyr Thr Gly Val Pro Ser Arg Phe
                645                 650                 655

Ser Gly Ser Gly Ser Gly Thr Asp Phe Thr Leu Thr Ile Ser Ser Leu
            660                 665                 670

Gln Pro Glu Asp Phe Ala Thr Tyr Tyr Cys Gln Gln Tyr Tyr Ile Tyr
        675                 680                 685

Pro Tyr Thr Phe Gly Gln Gly Thr Lys Val Glu Ile Lys
    690                 695                 700


<210> SEQ ID NO 41
<211> LENGTH: 120
<212> TYPE: PRT
<213> ORGANISM: Artificial Sequence
<220> FEATURE:
<223> OTHER INFORMATION: Synthesized

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120


<210> SEQ ID NO 42
<211> LENGTH: 241
<212> TYPE: PRT
<213> ORGANISM: Artificial Sequence
<220> FEATURE:
<223> OTHER INFORMATION: Synthesized

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
```

-continued

```
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Lys Ala Ser
145                 150                 155                 160

Gln Asp Val Ser Ile Gly Val Ala Trp Tyr Gln Gln Lys Pro Gly Lys
                165                 170                 175

Ala Pro Lys Leu Leu Ile Tyr Ser Ala Ser Tyr Arg Tyr Thr Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Tyr Tyr Ile Tyr Pro Tyr Thr Phe Gly Gln Gly Thr Lys Val Glu Ile
225                 230                 235                 240

Lys
```

<210> SEQ ID NO 43
<211> LENGTH: 642
<212> TYPE: DNA
<213> ORGANISM: Artificial Sequence
<220> FEATURE:
<223> OTHER INFORMATION: Synthesized

<400> SEQUENCE: 43

```
gacatccaga tgacacaatc tcctagcagt ctgagcgcaa gtgttggaga tcgtgtcacc      60

atcacatgca aggccagcca ggatgtgagc attggagtcg cctggtatca gcagaaaccc     120

ggcaaggcac ccaagctgct gatctactcg gccagttaca gatacactgg cgtaccttcg     180

aggtttagtg gtagcggttc tggaaccgat ttcaccctca ccattagctc cctccaaccc     240

gaggacttcg ccacctacta ctgccagcaa tactacatct acccttacac gttcggccaa     300

ggcactaagg tcgagattaa acgtacggtg gctgcaccat ctgtcttcat cttcccgcca     360

tctgatgagc agttgaaatc tggaactgcc tctgttgtgt gcctgctgaa taacttctat     420

cccagagagg ccaaagtaca gtggaaggtg gataacgccc tccaatcggg taactcccag     480

gagagtgtca cagagcagga cagcaaggac agcacctaca gcctcagcag caccctgacg     540

ctgagcaaag cagactacga gaaacacaaa gtctacgcct gcgaagtcac ccatcagggc     600

ctgagctcgc ccgtcacaaa gagcttcaac aggggagagt gt                        642
```

<210> SEQ ID NO 44
<211> LENGTH: 324
<212> TYPE: DNA

<213> ORGANISM: Artificial Sequence
<220> FEATURE:
<223> OTHER INFORMATION: Synthesized

<400> SEQUENCE: 44
gacatccaga tgacacaatc tcctagcagt ctgagcgcaa gtgttggaga tcgtgtcacc 60
atcacatgca aggccagcca ggatgtgagc attggagtcg cctggtatca gcagaaaccc 120
ggcaaggcac ccaagctgct gatctactcg gccagttaca gatacactgg cgtaccttcg 180
aggtttagtg gtagcggttc tggaaccgat ttcaccctca ccattagctc cctccaaccc 240
gaggacttcg ccacctacta ctgccagcaa tactacatct acccttacac gttcggccaa 300
ggcactaagg tcgagattaa acgt 324

<210> SEQ ID NO 45
<211> LENGTH: 214
<212> TYPE: PRT
<213> ORGANISM: Artificial Sequence
<220> FEATURE:
<223> OTHER INFORMATION: Synthesized

<400> SEQUENCE: 45

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Val Ser Ile Gly
20 25 30

Val Ala Trp Tyr Gln Gln Lys Pro Gly Lys Ala Pro Lys Leu Leu Ile
35 40 45

Tyr Ser Ala Ser Tyr Arg Tyr Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Tyr Ile Tyr Pro Tyr
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 46
<211> LENGTH: 107
<212> TYPE: PRT
<213> ORGANISM: Artificial Sequence
<220> FEATURE:
<223> OTHER INFORMATION: Synthesized

<400> SEQUENCE: 46

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105


<210> SEQ ID NO 47
<211> LENGTH: 2163
<212> TYPE: DNA
<213> ORGANISM: Artificial Sequence
<220> FEATURE:
<223> OTHER INFORMATION: Synthesized

<400> SEQUENCE: 47

gaagtgcagc tcgtcgaaag cggtggcgga ctggttcagc ccggtggttc tctgcggctg      60

tcttgtgctg cctcgggttt cacgttcact gactacacaa tggactgggt gcgtcaggct     120

cctggaaagg gattggagtg ggtagccgac gttaatccaa actccggcgg gagcatctac     180

aaccagaggt tcaaggggag gttcactctg agcgtggatc gctccaagaa cacgctgtac     240

ctccagatga actctctcag ggccgaggac acggctgttt actattgcgc gaggaacctg     300

ggtccttcct tctacttcga ctactgggga cagggaaccc tggtgaccgt cagctccgct     360

agcaccaagg gcccatcggt cttccccctg gcaccctcct ccaagagcac ctctgggggc     420

acagcggccc tgggctgcct ggtcaaggac tacttccccg aaccggtgac ggtgtcgtgg     480

aactcaggcg ccctgaccag cggcgtgcac accttcccgg ctgtcctaca gtcctcagga     540

ctctactccc tcagcagcgt ggtgaccgtg ccctccagca gcttgggcac ccagacctac     600

atctgcaacg tgaatcacaa gcccagcaac accaaggtgg acaagagagt tgagcccaaa     660

tcttgtgaca aaactcacac atgcccaccg tgcccagcac ctgaactcct ggggggaccg     720

tcagtcttcc tcttcccccc aaaacccaag gacaccctca tgatctcccg gacccctgag     780

gtcacatgcg tggtggtgga cgtgagccac gaagaccctg aggtcaagtt caactggtac     840

gtggacggcg tggaggtgca taatgccaag acaaagccgc gggaggagca gtacaacagc     900

acgtaccgtg tggtcagcgt cctcaccgtc ctgcaccagg actggctgaa tggcaaggag     960

tacaagtgca aggtctccaa caaagccctc ccagccccca tcgagaaaac catctccaaa    1020

gccaaagggc agccccgaga accacaggtg tacaccctgc ccccatcccg ggaggagatg    1080

accaagaacc aggtcagcct gacctgcctg gtcaaaggct tctatcccag cgacatcgcc    1140

gtggagtggg agagcaatgg gcagccggag aacaactaca agaccacgcc tcccgtgctg    1200

gactccgacg gctccttctt cctctatagc aagctcaccg tggacaagag caggtggcag    1260

caggggaacg tcttctcatg ctccgtgatg catgaggctc tgcacaacca ctacacgcag    1320

aagagcctct ccctgtctcc gggtaaagga ggcgggggtt ccggcggagg tggctcagga    1380

ggcggagggt caggggggagg tggctccggc ggtggaggat ccggcggtgg tggatcagag    1440
```

gttcagctgg tggagtctgg cggtggcctg gtgcagccag ggggctcact ccgtttgtcc 1500
tgtgcagctt ctggcttcaa cattaaagac acctatatac actgggtgcg tcaggccccg 1560
ggtaagggcc tggaatgggt tgcaaggatt tatcctacga atggttatac tagatatgcc 1620
gatagcgtca agggccgttt cactataagc gcagacacat ccaaaaacac agcctacctg 1680
cagatgaaca gcctgcgtgc tgaggacact gccgtctatt attgttctag atggggaggg 1740
gacggcttct atgctatgga ctactggggt caaggaaccc tggtcaccgt ctcctcgggt 1800
ggaggcggtt caggcggagg tggttccggc ggtggcggct ccgatatcca gatgacccag 1860
tccccgagct ccctgtccgc ctctgtgggc gatagggtca ccatcacctg ccgtgccagt 1920
caggatgtga atactgctgt agcctggtat caacagaaac caggaaaagc tccgaaacta 1980
ctgatttact cggcatcctt cctctactct ggagtccctt ctcgcttctc tggctccaga 2040
tctgggacgg atttcactct gaccatcagc agtctgcagc cggaagactt cgcaacttat 2100
tactgtcagc aacattatac tactcctccc acgttcggac agggtaccaa ggtggagatc 2160
aaa 2163

<210> SEQ ID NO 48
<211> LENGTH: 357
<212> TYPE: DNA
<213> ORGANISM: Artificial Sequence
<220> FEATURE:
<223> OTHER INFORMATION: Synthesized

<400> SEQUENCE: 48
gaagtgcagc tcgtcgaaag cggtggcgga ctggttcagc ccggtggttc tctgcggctg 60
tcttgtgctg cctcgggttt cacgttcact gactacacaa tggactgggt gcgtcaggct 120
cctggaaagg gattggagtg ggtagccgac gttaatccaa actccggcgg gagcatctac 180
aaccagaggt tcaaggggag gttcactctg agcgtggatc gctccaagaa cacgctgtac 240
ctccagatga actctctcag ggccgaggac acggctgttt actattgcgc gaggaacctg 300
ggtccttcct tctacttcga ctactgggga cagggaaccc tggtgaccgt cagctcc 357

<210> SEQ ID NO 49
<211> LENGTH: 726
<212> TYPE: DNA
<213> ORGANISM: Artificial Sequence
<220> FEATURE:
<223> OTHER INFORMATION: Synthesized

<400> SEQUENCE: 49
gaggttcagc tggtggagtc tggcggtggc ctggtgcagc cagggggctc actccgtttg 60
tcctgtgcag cttctggctt caacattaaa gacacctata tacactgggt gcgtcaggcc 120
ccgggtaagg gcctggaatg ggttgcaagg atttatccta cgaatggtta tactagatat 180
gccgatagcg tcaagggccg tttcactata agcgcagaca catccaaaaa cacagcctac 240
ctgcagatga acagcctgcg tgctgaggac actgccgtct attattgttc tagatgggga 300
ggggacggct tctatgctat ggactactgg ggtcaaggaa ccctggtcac cgtctcctcg 360
ggtggaggcg gttcaggcgg aggtggttcc ggcggtggcg gctccgatat ccagatgacc 420
cagtccccga gctccctgtc cgcctctgtg ggcgataggg tcaccatcac ctgccgtgcc 480
agtcaggatg tgaatactgc tgtagcctgg tatcaacaga aaccaggaaa agctccgaaa 540
ctactgattt actcggcatc cttcctctac tctggagtcc cttctcgctt ctctggctcc 600

-continued

```
agatctggga cggatttcac tctgaccatc agcagtctgc agccggaaga cttcgcaact    660

tattactgtc agcaacatta tactactcct cccacgttcg gacagggtac caaggtggag    720

atcaaa                                                               726


<210> SEQ ID NO 50
<211> LENGTH: 721
<212> TYPE: PRT
<213> ORGANISM: Artificial Sequence
<220> FEATURE:
<223> OTHER INFORMATION: Synthesized

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335
```

```
Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Gly Gly Gly Ser Gly Gly Gly Gly Ser Gly Gly Gly Gly Ser
    450                 455                 460

Gly Gly Gly Gly Ser Gly Gly Gly Gly Ser Gly Gly Gly Gly Ser Glu
465                 470                 475                 480

Val Gln Leu Val Glu Ser Gly Gly Gly Leu Val Gln Pro Gly Gly Ser
                485                 490                 495

Leu Arg Leu Ser Cys Ala Ala Ser Gly Phe Asn Ile Lys Asp Thr Tyr
            500                 505                 510

Ile His Trp Val Arg Gln Ala Pro Gly Lys Gly Leu Glu Trp Val Ala
        515                 520                 525

Arg Ile Tyr Pro Thr Asn Gly Tyr Thr Arg Tyr Ala Asp Ser Val Lys
    530                 535                 540

Gly Arg Phe Thr Ile Ser Ala Asp Thr Ser Lys Asn Thr Ala Tyr Leu
545                 550                 555                 560

Gln Met Asn Ser Leu Arg Ala Glu Asp Thr Ala Val Tyr Tyr Cys Ser
                565                 570                 575

Arg Trp Gly Gly Asp Gly Phe Tyr Ala Met Asp Tyr Trp Gly Gln Gly
            580                 585                 590

Thr Leu Val Thr Val Ser Ser Gly Gly Gly Gly Ser Gly Gly Gly Gly
        595                 600                 605

Ser Gly Gly Gly Gly Ser Asp Ile Gln Met Thr Gln Ser Pro Ser Ser
    610                 615                 620

Leu Ser Ala Ser Val Gly Asp Arg Val Thr Ile Thr Cys Arg Ala Ser
625                 630                 635                 640

Gln Asp Val Asn Thr Ala Val Ala Trp Tyr Gln Gln Lys Pro Gly Lys
                645                 650                 655

Ala Pro Lys Leu Leu Ile Tyr Ser Ala Ser Phe Leu Tyr Ser Gly Val
            660                 665                 670

Pro Ser Arg Phe Ser Gly Ser Arg Ser Gly Thr Asp Phe Thr Leu Thr
        675                 680                 685

Ile Ser Ser Leu Gln Pro Glu Asp Phe Ala Thr Tyr Tyr Cys Gln Gln
    690                 695                 700

His Tyr Thr Thr Pro Pro Thr Phe Gly Gln Gly Thr Lys Val Glu Ile
705                 710                 715                 720

Lys
```

<210> SEQ ID NO 51
<211> LENGTH: 642
<212> TYPE: DNA
<213> ORGANISM: Artificial Sequence -continued
<220> FEATURE:
<223> OTHER INFORMATION: Synthesized

<400> SEQUENCE: 51
gatatccaga tgacccagtc cccgagctcc ctgtccgcct ctgtgggcga tagggtcacc 60
atcacctgcc gtgccagtca ggatgtgaat actgctgtag cctggtatca acagaaacca 120
ggaaaagctc cgaaactact gatttactcg gcatccttcc tctactctgg agtcccttct 180
cgcttctctg gctccagatc tgggacggat ttcactctga ccatcagcag tctgcagccg 240
gaagacttcg caacttatta ctgtcagcaa cattatacta ctcctcccac gttcggacag 300
ggtaccaagg tggagatcaa acgtacggtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 52
<211> LENGTH: 321
<212> TYPE: DNA
<213> ORGANISM: Artificial Sequence
<220> FEATURE:
<223> OTHER INFORMATION: Synthesized

<400> SEQUENCE: 52
gatatccaga tgacccagtc cccgagctcc ctgtccgcct ctgtgggcga tagggtcacc 60
atcacctgcc gtgccagtca ggatgtgaat actgctgtag cctggtatca acagaaacca 120
ggaaaagctc cgaaactact gatttactcg gcatccttcc tctactctgg agtcccttct 180
cgcttctctg gctccagatc tgggacggat ttcactctga ccatcagcag tctgcagccg 240
gaagacttcg caacttatta ctgtcagcaa cattatacta ctcctcccac gttcggacag 300
ggtaccaagg tggagatcaa a 321

<210> SEQ ID NO 53
<211> LENGTH: 214
<212> TYPE: PRT
<213> ORGANISM: Artificial Sequence
<220> FEATURE:
<223> OTHER INFORMATION: Synthesized

<400> SEQUENCE: 53

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Asn Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln His Tyr Thr Thr Pro Pro
85 90 95

Thr Phe Gly Gln Gly Thr Lys Val Glu Ile Lys Arg Thr Val Ala Ala
100 105 110

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 54
<211> LENGTH: 107
<212> TYPE: PRT
<213> ORGANISM: Artificial Sequence
<220> FEATURE:
<223> OTHER INFORMATION: Synthesized

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105


<210> SEQ ID NO 55
<211> LENGTH: 2163
<212> TYPE: DNA
<213> ORGANISM: Artificial Sequence
<220> FEATURE:
<223> OTHER INFORMATION: Synthesized

<400> SEQUENCE: 55

gaggttcagc tggtggagtc tggcggtggc ctggtgcagc caggggggctc actccgtttg      60

tcctgtgcag cttctggctt caacattaaa gacacctata tacactgggt gcgtcaggcc     120

ccgggtaagg gcctggaatg ggttgcaagg atttatccta cgaatggtta tactagatat     180

gccgatagcg tcaagggccg tttcactata agcgcagaca catccaaaaa cacagcctac     240

ctgcagatga acagcctgcg tgctgaggac actgccgtct attattgttc tagatgggga     300

ggggacggct tctatgctat ggactactgg ggtcaaggaa ccctggtcac cgtctcctcg     360

gctagcacca agggcccatc ggtcttcccc ctggcaccct cctccaagag cacctctggg     420

ggcacagcgg ccctgggctg cctggtcaag gactacttcc ccgaaccggt gacggtgtcg     480
```

-continued

```
tggaactcag gcgccctgac cagcggcgtg cacaccttcc cggctgtcct acagtcctca    540

ggactctact ccctcagcag cgtggtgacc gtgccctcca gcagcttggg cacccagacc    600

tacatctgca acgtgaatca caagcccagc aacaccaagg tggacaagag agttgagccc    660

aaatcttgtg acaaaactca cacatgccca ccgtgcccag cacctgaact cctgggggga    720

ccgtcagtct tcctcttccc cccaaaaccc aaggacaccc tcatgatctc ccggacccct    780

gaggtcacat gcgtggtggt ggacgtgagc cacgaagacc ctgaggtcaa gttcaactgg    840

tacgtggacg gcgtggaggt gcataatgcc aagacaaagc cgcgggagga gcagtacaac    900

agcacgtacc gtgtggtcag cgtcctcacc gtcctgcacc aggactggct gaatggcaag    960

gagtacaagt gcaaggtctc caacaaagcc ctcccagccc ccatcgagaa aaccatctcc   1020

aaagccaaag ggcagccccg agaaccacag gtgtacaccc tgcccccatc ccgggaggag   1080

atgaccaaga accaggtcag cctgacctgc ctggtcaaag gcttctatcc cagcgacatc   1140

gccgtggagt gggagagcaa tgggcagccg gagaacaact acaagaccac gcctcccgtg   1200

ctggactccg acggctcctt cttcctctat agcaagctca ccgtggacaa gagcaggtgg   1260

cagcagggga acgtcttctc atgctccgtg atgcatgagg ctctgcacaa ccactacacg   1320

cagaagagcc tctccctgtc tccgggtaaa ggaggcgggg gttccggcgg aggtggctca   1380

ggaggcggag ggtcaggggg aggtggctcc ggcggtggag gatccggcgg tggtggatca   1440

gaagtgcagc tcgtcgaaag cggtggcgga ctggttcagc ccggtggttc tctgcggctg   1500

tcttgtgctg cctcgggttt cacgttcact gactacacaa tggactgggt gcgtcaggct   1560

cctggaaagg gattggagtg ggtagccgac gttaatccaa actccggcgg gagcatctac   1620

aaccagaggt tcaaggggag gttcactctg agcgtggatc gctccaagaa cacgctgtac   1680

ctccagatga actctctcag ggccgaggac acggctgttt actattgcgc gaggaacctg   1740

ggtccttcct tctacttcga ctactgggga cagggaaccc tggtgaccgt cagctccggt   1800

ggaggcggtt caggcggagg tggttccggc ggtggcggct ccgacatcca gatgacacaa   1860

tctcctagca gtctgagcgc aagtgttgga gatcgtgtca ccatcacatg caaggccagc   1920

caggatgtga gcattggagt cgcctggtat cagcagaaac ccggcaaggc acccaagctg   1980

ctgatctact cggccagtta cagatacact ggcgtacctt cgaggtttag tggtagcggt   2040

tctggaaccg atttcaccct caccattagc tccctccaac ccgaggactt cgccacctac   2100

tactgccagc aatactacat ctacccttac acgttcggcc aaggcactaa ggtcgagatt   2160

aaa                                                                 2163
```

```
<210> SEQ ID NO 56
<211> LENGTH: 360
<212> TYPE: DNA
<213> ORGANISM: Artificial Sequence
<220> FEATURE:
<223> OTHER INFORMATION: Synthesized

<400> SEQUENCE: 56

gaggttcagc tggtggagtc tggcggtggc ctggtgcagc caggggggctc actccgtttg     60

tcctgtgcag cttctggctt caacattaaa gacacctata tacactgggt gcgtcaggcc    120

ccgggtaagg gcctggaatg ggttgcaagg atttatccta cgaatggtta tactagatat    180

gccgatagcg tcaagggccg tttcactata agcgcagaca catccaaaaa cacagcctac    240

ctgcagatga acagcctgcg tgctgaggac actgccgtct attattgttc tagatgggga    300

ggggacggct tctatgctat ggactactgg ggtcaaggaa ccctggtcac cgtctcctcg    360
```

<210> SEQ ID NO 57
<211> LENGTH: 723
<212> TYPE: DNA
<213> ORGANISM: Artificial Sequence
<220> FEATURE:
<223> OTHER INFORMATION: Synthesized

<400> SEQUENCE: 57
gaagtgcagc tcgtcgaaag cggtggcgga ctggttcagc ccggtggttc tctgcggctg 60
tcttgtgctg cctcgggttt cacgttcact gactacacaa tggactgggt gcgtcaggct 120
cctggaaagg gattggagtg ggtagccgac gttaatccaa actccggcgg gagcatctac 180
aaccagaggt tcaaggggag gttcactctg agcgtggatc gctccaagaa cacgctgtac 240
ctccagatga actctctcag ggccgaggac acggctgttt actattgcgc gaggaacctg 300
ggtccttcct tctacttcga ctactgggga cagggaaccc tggtgaccgt cagctccggt 360
ggaggcggtt caggcggagg tggttccggc ggtggcggct ccgacatcca gatgacacaa 420
tctcctagca gtctgagcgc aagtgttgga gatcgtgtca ccatcacatg caaggccagc 480
caggatgtga gcattggagt cgcctggtat cagcagaaac ccggcaaggc acccaagctg 540
ctgatctact cggccagtta cagatacact ggcgtacctt cgaggtttag tggtagcggt 600
tctggaaccg atttcaccct caccattagc tccctccaac ccgaggactt cgccacctac 660
tactgccagc aatactacat ctacccttac acgttcggcc aaggcactaa ggtcgagatt 720
aaa 723

<210> SEQ ID NO 58
<211> LENGTH: 721
<212> TYPE: PRT
<213> ORGANISM: Artificial Sequence
<220> FEATURE:
<223> OTHER INFORMATION: Synthesized

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

-continued

```
Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Gly Gly Gly Gly Ser Gly Gly Gly Gly Ser Gly Gly Gly Gly
    450                 455                 460

Ser Gly Gly Gly Gly Ser Gly Gly Gly Gly Ser Gly Gly Gly Gly Ser
465                 470                 475                 480

Glu Val Gln Leu Val Glu Ser Gly Gly Gly Leu Val Gln Pro Gly Gly
                485                 490                 495

Ser Leu Arg Leu Ser Cys Ala Ala Ser Gly Phe Thr Phe Thr Asp Tyr
            500                 505                 510

Thr Met Asp Trp Val Arg Gln Ala Pro Gly Lys Gly Leu Glu Trp Val
        515                 520                 525

Ala Asp Val Asn Pro Asn Ser Gly Gly Ser Ile Tyr Asn Gln Arg Phe
    530                 535                 540

Lys Gly Arg Phe Thr Leu Ser Val Asp Arg Ser Lys Asn Thr Leu Tyr
545                 550                 555                 560

Leu Gln Met Asn Ser Leu Arg Ala Glu Asp Thr Ala Val Tyr Tyr Cys
                565                 570                 575

Ala Arg Asn Leu Gly Pro Ser Phe Tyr Phe Asp Tyr Trp Gly Gln Gly
            580                 585                 590
```

```
Thr Leu Val Thr Val Ser Ser Gly Gly Gly Gly Ser Gly Gly Gly Gly
        595                 600                 605

Ser Gly Gly Gly Gly Ser Asp Ile Gln Met Thr Gln Ser Pro Ser Ser
    610                 615                 620

Leu Ser Ala Ser Val Gly Asp Arg Val Thr Ile Thr Cys Lys Ala Ser
625                 630                 635                 640

Gln Asp Val Ser Ile Gly Val Ala Trp Tyr Gln Gln Lys Pro Gly Lys
                645                 650                 655

Ala Pro Lys Leu Leu Ile Tyr Ser Ala Ser Tyr Arg Tyr Thr Gly Val
            660                 665                 670

Pro Ser Arg Phe Ser Gly Ser Gly Ser Gly Thr Asp Phe Thr Leu Thr
        675                 680                 685

Ile Ser Ser Leu Gln Pro Glu Asp Phe Ala Thr Tyr Tyr Cys Gln Gln
    690                 695                 700

Tyr Tyr Ile Tyr Pro Tyr Thr Phe Gly Gln Gly Thr Lys Val Glu Ile
705                 710                 715                 720

Lys


<210> SEQ ID NO 59
<211> LENGTH: 120
<212> TYPE: PRT
<213> ORGANISM: Artificial Sequence
<220> FEATURE:
<223> OTHER INFORMATION: Synthesized

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120


<210> SEQ ID NO 60
<211> LENGTH: 241
<212> TYPE: PRT
<213> ORGANISM: Artificial Sequence
<220> FEATURE:
<223> OTHER INFORMATION: Synthesized

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45
```

-continued

```
Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Lys Ala Ser
145                 150                 155                 160

Gln Asp Val Ser Ile Gly Val Ala Trp Tyr Gln Gln Lys Pro Gly Lys
                165                 170                 175

Ala Pro Lys Leu Leu Ile Tyr Ser Ala Ser Tyr Arg Tyr Thr Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Tyr Tyr Ile Tyr Pro Tyr Thr Phe Gly Gln Gly Thr Lys Val Glu Ile
225                 230                 235                 240

Lys
```

<210> SEQ ID NO 61
<211> LENGTH: 1467
<212> TYPE: DNA
<213> ORGANISM: Artificial Sequence
<220> FEATURE:
<223> OTHER INFORMATION: Synthesized

<400> SEQUENCE: 61

```
gagcccaaat cttgtgacaa aactcacaca tgcccaccgt gcccagcacc tgaactcctg      60

gggggaccgt cagtcttcct cttcccccca aaacccaagg acaccctcat gatctcccgg     120

acccctgagg tcacatgcgt ggtggtggac gtgagccacg aagaccctga ggtcaagttc     180

aactggtacg tggacggcgt ggaggtgcat aatgccaaga caaagccgcg ggaggagcag     240

tacaacagca cgtaccgtgt ggtcagcgtc ctcaccgtcc tgcaccagga ctggctgaat     300

ggcaaggagt acaagtgcaa ggtctccaac aaagccctcc cagcccccat cgagaaaacc     360

atctccaaag ccaaagggca gccccgagaa ccacaggtgt acaccctgcc cccatcccgg     420

gaggagatga ccaagaacca ggtcagcctg acctgcctgg tcaaaggctt ctatcccagc     480

gacatcgccg tggagtggga gagcaatggg cagccggaga acaactacaa gaccacgcct     540

cccgtgctgg actccgacgg ctccttcttc ctctatagca agctcaccgt ggacaagagc     600

aggtggcagc aggggaacgt cttctcatgc tccgtgatgc atgaggctct gcacaaccac     660

tacacgcaga agagcctctc cctgtctccg ggtaaagggg gaggtggctc cggcggtgga     720

ggatccggcg gtggtggatc agaggttcag ctggtggagt ctggcggtgg cctggtgcag     780

ccagggggct cactccgttt gtcctgtgca gcttctggct tcaacattaa agacacctat     840

atacactggg tgcgtcaggc cccgggtaag ggcctggaat gggttgcaag gatttatcct     900

acgaatggtt atactagata tgccgatagc gtcaagggcc gtttcactat aagcgcagac     960
```

-continued

```
acatccaaaa acacagccta cctgcagatg aacagcctgc gtgctgagga cactgccgtc   1020

tattattgtt ctagatgggg aggggacggc ttctatgcta tggactactg gggtcaagga   1080

accctggtca ccgtctcctc gggtggaggc ggttcaggcg gaggtggttc cggcggtggc   1140

ggctccgata tccagatgac ccagtccccg agctccctgt ccgcctctgt gggcgatagg   1200

gtcaccatca cctgccgtgc cagtcaggat gtgaatactg ctgtagcctg gtatcaacag   1260

aaaccaggaa aagctccgaa actactgatt tactcggcat ccttcctcta ctctggagtc   1320

ccttctcgct tctctggctc cagatctggg acggatttca ctctgaccat cagcagtctg   1380

cagccggaag acttcgcaac ttattactgt cagcaacatt atactactcc tcccacgttc   1440

ggacagggta ccaaggtgga gatcaaa                                       1467
```

```
<210> SEQ ID NO 62
<211> LENGTH: 489
<212> TYPE: PRT
<213> ORGANISM: Artificial Sequence
<220> FEATURE:
<223> OTHER INFORMATION: Synthesized

<400> SEQUENCE: 62

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Gly Gly Gly Gly Ser Gly Gly Gly
225                 230                 235                 240

Gly Ser Gly Gly Gly Gly Ser Glu Val Gln Leu Val Glu Ser Gly Gly
                245                 250                 255

Gly Leu Val Gln Pro Gly Gly Ser Leu Arg Leu Ser Cys Ala Ala Ser
            260                 265                 270
```

```
Gly Phe Asn Ile Lys Asp Thr Tyr Ile His Trp Val Arg Gln Ala Pro
        275                 280                 285

Gly Lys Gly Leu Glu Trp Val Ala Arg Ile Tyr Pro Thr Asn Gly Tyr
    290                 295                 300

Thr Arg Tyr Ala Asp Ser Val Lys Gly Arg Phe Thr Ile Ser Ala Asp
305                 310                 315                 320

Thr Ser Lys Asn Thr Ala Tyr Leu Gln Met Asn Ser Leu Arg Ala Glu
                325                 330                 335

Asp Thr Ala Val Tyr Tyr Cys Ser Arg Trp Gly Gly Asp Gly Phe Tyr
            340                 345                 350

Ala Met Asp Tyr Trp Gly Gln Gly Thr Leu Val Thr Val Ser Ser Gly
        355                 360                 365

Gly Gly Gly Ser Gly Gly Gly Gly Ser Gly Gly Gly Gly Ser Asp Ile
    370                 375                 380

Gln Met Thr Gln Ser Pro Ser Ser Leu Ser Ala Ser Val Gly Asp Arg
385                 390                 395                 400

Val Thr Ile Thr Cys Arg Ala Ser Gln Asp Val Asn Thr Ala Val Ala
                405                 410                 415

Trp Tyr Gln Gln Lys Pro Gly Lys Ala Pro Lys Leu Leu Ile Tyr Ser
            420                 425                 430

Ala Ser Phe Leu Tyr Ser Gly Val Pro Ser Arg Phe Ser Gly Ser Arg
        435                 440                 445

Ser Gly Thr Asp Phe Thr Leu Thr Ile Ser Ser Leu Gln Pro Glu Asp
    450                 455                 460

Phe Ala Thr Tyr Tyr Cys Gln Gln His Tyr Thr Thr Pro Pro Thr Phe
465                 470                 475                 480

Gly Gln Gly Thr Lys Val Glu Ile Lys
                485


<210> SEQ ID NO 63
<211> LENGTH: 242
<212> TYPE: PRT
<213> ORGANISM: Artificial Sequence
<220> FEATURE:
<223> OTHER INFORMATION: Synthesized

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140
```

```
Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln His Tyr Thr Thr Pro Pro Thr Phe Gly Gln Gly Thr Lys Val Glu
225                 230                 235                 240

Ile Lys


<210> SEQ ID NO 64
<211> LENGTH: 1482
<212> TYPE: DNA
<213> ORGANISM: Artificial Sequence
<220> FEATURE:
<223> OTHER INFORMATION: Synthesized

<400> SEQUENCE: 64

gagcccaaat cttgtgacaa aactcacaca tgcccaccgt gcccagcacc tgaactcctg      60

gggggaccgt cagtcttcct cttcccccca aaacccaagg acaccctcat gatctcccgg     120

acccctgagg tcacatgcgt ggtggtggac gtgagccacg aagaccctga ggtcaagttc     180

aactggtacg tggacggcgt ggaggtgcat aatgccaaga caaagccgcg ggaggagcag     240

tacaacagca cgtaccgtgt ggtcagcgtc ctcaccgtcc tgcaccagga ctggctgaat     300

ggcaaggagt acaagtgcaa ggtctccaac aaagccctcc cagcccccat cgagaaaacc     360

atctccaaag ccaaagggca gccccgagaa ccacaggtgt acaccctgcc cccatcccgg     420

gaggagatga ccaagaacca ggtcagcctg acctgcctgg tcaaaggctt ctatcccagc     480

gacatcgccg tggagtggga gagcaatggg cagccggaga acaactacaa gaccacgcct     540

cccgtgctgg actccgacgg ctccttcttc ctctatagca agctcaccgt ggacaagagc     600

aggtggcagc aggggaacgt cttctcatgc tccgtgatgc atgaggctct gcacaaccac     660

tacacgcaga agagcctctc cctgtctccg ggtaaaggag gcggagggtc agggggaggt     720

ggctccggcg gtggaggatc cggcggtggt ggatcagagg ttcagctggt ggagtctggc     780

ggtggcctgg tgcagccagg gggctcactc cgtttgtcct gtgcagcttc tggcttcaac     840

attaaagaca cctatataca ctgggtgcgt caggccccgg gtaagggcct ggaatgggtt     900

gcaaggattt atcctacgaa tggttatact agatatgccg atagcgtcaa gggccgtttc     960

actataagcg cagacacatc caaaaacaca gcctacctgc agatgaacag cctgcgtgct    1020

gaggacactg ccgtctatta ttgttctaga tggggagggg acggcttcta tgctatggac    1080

tactggggtc aaggaaccct ggtcaccgtc tcctcgggtg gaggcggttc aggcggaggt    1140

ggttccggcg gtggcggctc cgatatccag atgacccagt ccccgagctc cctgtccgcc    1200

tctgtgggcg atagggtcac catcacctgc cgtgccagtc aggatgtgaa tactgctgta    1260

gcctggtatc aacagaaacc aggaaaagct ccgaaactac tgatttactc ggcatccttc    1320

ctctactctg gagtcccttc tcgcttctct ggctccagat ctgggacgga tttcactctg    1380

accatcagca gtctgcagcc ggaagacttc gcaacttatt actgtcagca acattatact    1440
```

-continued actcctccca cgttcggaca gggtaccaag gtggagatca aa 1482

<210> SEQ ID NO 65
<211> LENGTH: 494
<212> TYPE: PRT
<213> ORGANISM: Artificial Sequence
<220> FEATURE:
<223> OTHER INFORMATION: Synthesized

<400> SEQUENCE: 65

Glu Pro Lys Ser Cys Asp Lys Thr His Thr Cys Pro Pro Cys Pro Ala
1 5 10 15

Pro Glu Leu Leu Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Pro Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Thr Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Lys Gly Gly Gly Gly Ser Gly Gly Gly
225 230 235 240

Gly Ser Gly Gly Gly Gly Ser Gly Gly Gly Gly Ser Glu Val Gln Leu
245 250 255

Val Glu Ser Gly Gly Gly Leu Val Gln Pro Gly Gly Ser Leu Arg Leu
260 265 270

Ser Cys Ala Ala Ser Gly Phe Asn Ile Lys Asp Thr Tyr Ile His Trp
275 280 285

Val Arg Gln Ala Pro Gly Lys Gly Leu Glu Trp Val Ala Arg Ile Tyr
290 295 300

Pro Thr Asn Gly Tyr Thr Arg Tyr Ala Asp Ser Val Lys Gly Arg Phe
305 310 315 320

Thr Ile Ser Ala Asp Thr Ser Lys Asn Thr Ala Tyr Leu Gln Met Asn
325 330 335

Ser Leu Arg Ala Glu Asp Thr Ala Val Tyr Tyr Cys Ser Arg Trp Gly
340 345 350

Gly Asp Gly Phe Tyr Ala Met Asp Tyr Trp Gly Gln Gly Thr Leu Val

```
        355                 360                 365

Thr Val Ser Ser Gly Gly Gly Gly Ser Gly Gly Gly Gly Ser Gly Gly
    370                 375                 380

Gly Gly Ser Asp Ile Gln Met Thr Gln Ser Pro Ser Ser Leu Ser Ala
385                 390                 395                 400

Ser Val Gly Asp Arg Val Thr Ile Thr Cys Arg Ala Ser Gln Asp Val
                405                 410                 415

Asn Thr Ala Val Ala Trp Tyr Gln Gln Lys Pro Gly Lys Ala Pro Lys
            420                 425                 430

Leu Leu Ile Tyr Ser Ala Ser Phe Leu Tyr Ser Gly Val Pro Ser Arg
        435                 440                 445

Phe Ser Gly Ser Arg Ser Gly Thr Asp Phe Thr Leu Thr Ile Ser Ser
    450                 455                 460

Leu Gln Pro Glu Asp Phe Ala Thr Tyr Tyr Cys Gln Gln His Tyr Thr
465                 470                 475                 480

Thr Pro Pro Thr Phe Gly Gln Gly Thr Lys Val Glu Ile Lys
                485                 490


<210> SEQ ID NO 66
<211> LENGTH: 242
<212> TYPE: PRT
<213> ORGANISM: Artificial Sequence
<220> FEATURE:
<223> OTHER INFORMATION: Synthesized

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln His Tyr Thr Thr Pro Pro Thr Phe Gly Gln Gly Thr Lys Val Glu
```

-continued 225 230 235 240

Ile Lys

<210> SEQ ID NO 67
<211> LENGTH: 1497
<212> TYPE: DNA
<213> ORGANISM: Artificial Sequence
<220> FEATURE:
<223> OTHER INFORMATION: Synthesized

<400> SEQUENCE: 67
gagcccaaat cttgtgacaa aactcacaca tgcccaccgt gcccagcacc tgaactcctg 60
gggggaccgt cagtcttcct cttcccccca aaacccaagg acaccctcat gatctcccgg 120
acccctgagg tcacatgcgt ggtggtggac gtgagccacg aagaccctga ggtcaagttc 180
aactggtacg tggacggcgt ggaggtgcat aatgccaaga caaagccgcg ggaggagcag 240
tacaacagca cgtaccgtgt ggtcagcgtc ctcaccgtcc tgcaccagga ctggctgaat 300
ggcaaggagt acaagtgcaa ggtctccaac aaagccctcc cagcccccat cgagaaaacc 360
atctccaaag ccaaagggca gccccgagaa ccacaggtgt acaccctgcc cccatcccgg 420
gaggagatga ccaagaacca ggtcagcctg acctgcctgg tcaaaggctt ctatcccagc 480
gacatcgccg tggagtggga gagcaatggg cagccggaga acaactacaa gaccacgcct 540
cccgtgctgg actccgacgg ctccttcttc ctctatagca agctcaccgt ggacaagagc 600
aggtggcagc aggggaacgt cttctcatgc tccgtgatgc atgaggctct gcacaaccac 660
tacacgcaga agagcctctc cctgtctccg ggtaaaggcg gaggtggctc aggaggcgga 720
gggtcagggg gaggtggctc cggcggtgga ggatccggcg gtggtggatc agaggttcag 780
ctggtggagt ctggcggtgg cctggtgcag ccagggggct cactccgttt gtcctgtgca 840
gcttctggct tcaacattaa agacacctat atacactggg tgcgtcaggc cccgggtaag 900
ggcctggaat gggttgcaag gatttatcct acgaatggtt atactagata tgccgatagc 960
gtcaagggcc gtttcactat aagcgcagac acatccaaaa acacagccta cctgcagatg 1020
aacagcctgc gtgctgagga cactgccgtc tattattgtt ctagatgggg aggggacggc 1080
ttctatgcta tggactactg gggtcaagga accctggtca ccgtctcctc gggtggaggc 1140
ggttcaggcg gaggtggttc cggcggtggc ggctccgata tccagatgac ccagtccccg 1200
agctccctgt ccgcctctgt gggcgatagg gtcaccatca cctgccgtgc cagtcaggat 1260
gtgaatactg ctgtagcctg gtatcaacag aaaccaggaa aagctccgaa actactgatt 1320
tactcggcat ccttcctcta ctctggagtc ccttctcgct tctctggctc cagatctggg 1380
acggatttca ctctgaccat cagcagtctg cagccggaag acttcgcaac ttattactgt 1440
cagcaacatt atactactcc tcccacgttc ggacagggta ccaaggtgga gatcaaa 1497

<210> SEQ ID NO 68
<211> LENGTH: 499
<212> TYPE: PRT
<213> ORGANISM: Artificial Sequence
<220> FEATURE:
<223> OTHER INFORMATION: Synthesized

<400> SEQUENCE: 68

Glu Pro Lys Ser Cys Asp Lys Thr His Thr Cys Pro Pro Cys Pro Ala
1 5 10 15

Pro Glu Leu Leu Gly Gly Pro Ser Val Phe Leu Phe Pro Pro Lys Pro
20 25 30

```
Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Gly Gly Gly Gly Ser Gly Gly Gly
225                 230                 235                 240

Gly Gly Gly Gly Gly Ser Gly Gly Gly Gly Ser Gly Gly Gly Gly Ser
                245                 250                 255

Ser Glu Val Gln Leu Val Glu Ser Gly Gly Gly Leu Val Gln Pro Gly
            260                 265                 270

Gly Ser Leu Arg Leu Ser Cys Ala Ala Ser Gly Phe Asn Ile Lys Asp
        275                 280                 285

Thr Tyr Ile His Trp Val Arg Gln Ala Pro Gly Lys Gly Leu Glu Trp
    290                 295                 300

Val Ala Arg Ile Tyr Pro Thr Asn Gly Tyr Thr Arg Tyr Ala Asp Ser
305                 310                 315                 320

Val Lys Gly Arg Phe Thr Ile Ser Ala Asp Thr Ser Lys Asn Thr Ala
                325                 330                 335

Tyr Leu Gln Met Asn Ser Leu Arg Ala Glu Asp Thr Ala Val Tyr Tyr
            340                 345                 350

Cys Ser Arg Trp Gly Gly Asp Gly Phe Tyr Ala Met Asp Tyr Trp Gly
        355                 360                 365

Gln Gly Thr Leu Val Thr Val Ser Ser Gly Gly Gly Gly Ser Gly Gly
    370                 375                 380

Gly Gly Ser Gly Gly Gly Gly Ser Asp Ile Gln Met Thr Gln Ser Pro
385                 390                 395                 400

Ser Ser Leu Ser Ala Ser Val Gly Asp Arg Val Thr Ile Thr Cys Arg
                405                 410                 415

Ala Ser Gln Asp Val Asn Thr Ala Val Ala Trp Tyr Gln Gln Lys Pro
            420                 425                 430

Gly Lys Ala Pro Lys Leu Leu Ile Tyr Ser Ala Ser Phe Leu Tyr Ser
        435                 440                 445
```

```
Gly Val Pro Ser Arg Phe Ser Gly Ser Arg Ser Gly Thr Asp Phe Thr
    450                 455                 460

Leu Thr Ile Ser Ser Leu Gln Pro Glu Asp Phe Ala Thr Tyr Tyr Cys
465                 470                 475                 480

Gln Gln His Tyr Thr Thr Pro Pro Thr Phe Gly Gln Gly Thr Lys Val
                485                 490                 495

Glu Ile Lys
```

<210> SEQ ID NO 69
<211> LENGTH: 242
<212> TYPE: PRT
<213> ORGANISM: Artificial Sequence
<220> FEATURE:
<223> OTHER INFORMATION: Synthesized

<400> SEQUENCE: 69

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln His Tyr Thr Thr Pro Pro Thr Phe Gly Gln Gly Thr Lys Val Glu
225                 230                 235                 240

Ile Lys
```

<210> SEQ ID NO 70
<211> LENGTH: 1512
<212> TYPE: DNA
<213> ORGANISM: Artificial Sequence
<220> FEATURE:
<223> OTHER INFORMATION: Synthesized

<400> SEQUENCE: 70

```
gagcccaaat cttgtgacaa aactcacaca tgcccaccgt gcccagcacc tgaactcctg     60
```

-continued

```
gggggaccgt cagtcttcct cttcccccca aaacccaagg acaccctcat gatctcccgg    120

acccctgagg tcacatgcgt ggtggtggac gtgagccacg aagaccctga ggtcaagttc    180

aactggtacg tggacggcgt ggaggtgcat aatgccaaga caaagccgcg ggaggagcag    240

tacaacagca cgtaccgtgt ggtcagcgtc ctcaccgtcc tgcaccagga ctggctgaat    300

ggcaaggagt acaagtgcaa ggtctccaac aaagccctcc cagcccccat cgagaaaacc    360

atctccaaag ccaaagggca gccccgagaa ccacaggtgt acaccctgcc cccatcccgg    420

gaggagatga ccaagaacca ggtcagcctg acctgcctgg tcaaaggctt ctatcccagc    480

gacatcgccg tggagtggga gagcaatggg cagccggaga acaactacaa gaccacgcct    540

cccgtgctgg actccgacgg ctccttcttc ctctatagca agctcaccgt ggacaagagc    600

aggtggcagc aggggaacgt cttctcatgc tccgtgatgc atgaggctct gcacaaccac    660

tacacgcaga agagcctctc cctgtctccg ggtaaaggag gcgggggttc cggcggaggt    720

ggctcaggag gcggagggtc agggggaggt ggctccggcg gtggaggatc cggcggtggt    780

ggatcagagg ttcagctggt ggagtctggc ggtggcctgg tgcagccagg gggctcactc    840

cgtttgtcct gtgcagcttc tggcttcaac attaaagaca cctatataca ctgggtgcgt    900

caggccccgg gtaagggcct ggaatgggtt gcaaggattt atcctacgaa tggttatact    960

agatatgccg atagcgtcaa gggccgtttc actataagcg cagacacatc caaaaacaca   1020

gcctacctgc agatgaacag cctgcgtgct gaggacactg ccgtctatta ttgttctaga   1080

tggggagggg acggcttcta tgctatggac tactggggtc aaggaaccct ggtcaccgtc   1140

tcctcgggtg gaggcggttc aggcggaggt ggttccggcg gtggcggctc cgatatccag   1200

atgacccagt ccccgagctc cctgtccgcc tctgtgggcg atagggtcac catcacctgc   1260

cgtgccagtc aggatgtgaa tactgctgta gcctggtatc aacagaaacc aggaaaagct   1320

ccgaaactac tgatttactc ggcatccttc ctctactctg gagtcccttc tcgcttctct   1380

ggctccagat ctgggacgga tttcactctg accatcagca gtctgcagcc ggaagacttc   1440

gcaacttatt actgtcagca acattatact actcctccca cgttcggaca gggtaccaag   1500

gtggagatca aa                                                       1512
```

<210> SEQ ID NO 71
<211> LENGTH: 504
<212> TYPE: PRT
<213> ORGANISM: Artificial Sequence
<220> FEATURE:
<223> OTHER INFORMATION: Synthesized

<400> SEQUENCE: 71

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95
```

-continued

```
Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Gly Gly Gly Gly Ser Gly Gly Gly
225                 230                 235                 240

Gly Ser Gly Gly Gly Gly Ser Gly Gly Gly Gly Ser Gly Gly Gly Gly
                245                 250                 255

Ser Gly Gly Gly Gly Ser Glu Val Gln Leu Val Glu Ser Gly Gly Gly
            260                 265                 270

Leu Val Gln Pro Gly Gly Ser Leu Arg Leu Ser Cys Ala Ala Ser Gly
        275                 280                 285

Phe Asn Ile Lys Asp Thr Tyr Ile His Trp Val Arg Gln Ala Pro Gly
    290                 295                 300

Lys Gly Leu Glu Trp Val Ala Arg Ile Tyr Pro Thr Asn Gly Tyr Thr
305                 310                 315                 320

Arg Tyr Ala Asp Ser Val Lys Gly Arg Phe Thr Ile Ser Ala Asp Thr
                325                 330                 335

Ser Lys Asn Thr Ala Tyr Leu Gln Met Asn Ser Leu Arg Ala Glu Asp
            340                 345                 350

Thr Ala Val Tyr Tyr Cys Ser Arg Trp Gly Gly Asp Gly Phe Tyr Ala
        355                 360                 365

Met Asp Tyr Trp Gly Gln Gly Thr Leu Val Thr Val Ser Ser Gly Gly
    370                 375                 380

Gly Gly Ser Gly Gly Gly Gly Ser Gly Gly Gly Gly Ser Asp Ile Gln
385                 390                 395                 400

Met Thr Gln Ser Pro Ser Ser Leu Ser Ala Ser Val Gly Asp Arg Val
                405                 410                 415

Thr Ile Thr Cys Arg Ala Ser Gln Asp Val Asn Thr Ala Val Ala Trp
            420                 425                 430

Tyr Gln Gln Lys Pro Gly Lys Ala Pro Lys Leu Leu Ile Tyr Ser Ala
        435                 440                 445

Ser Phe Leu Tyr Ser Gly Val Pro Ser Arg Phe Ser Gly Ser Arg Ser
    450                 455                 460

Gly Thr Asp Phe Thr Leu Thr Ile Ser Ser Leu Gln Pro Glu Asp Phe
465                 470                 475                 480

Ala Thr Tyr Tyr Cys Gln Gln His Tyr Thr Thr Pro Pro Thr Phe Gly
                485                 490                 495

Gln Gly Thr Lys Val Glu Ile Lys
            500
```

<210> SEQ ID NO 72
<211> LENGTH: 242
<212> TYPE: PRT
<213> ORGANISM: Artificial Sequence
<220> FEATURE:
<223> OTHER INFORMATION: Synthesized

<400> SEQUENCE: 72

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Asp Ile Gln Met Thr Gln Ser Pro Ser
130 135 140

Ser Leu Ser Ala Ser Val Gly Asp Arg Val Thr Ile Thr Cys Arg Ala
145 150 155 160

Ser Gln Asp Val Asn Thr Ala Val Ala Trp Tyr Gln Gln Lys Pro Gly
165 170 175

Lys Ala Pro Lys Leu Leu Ile Tyr Ser Ala Ser Phe Leu Tyr Ser Gly
180 185 190

Val Pro Ser Arg Phe Ser Gly Ser Arg Ser Gly Thr Asp Phe Thr Leu
195 200 205

Thr Ile Ser Ser Leu Gln Pro Glu Asp Phe Ala Thr Tyr Tyr Cys Gln
210 215 220

Gln His Tyr Thr Thr Pro Pro Thr Phe Gly Gln Gly Thr Lys Val Glu
225 230 235 240

Ile Lys

<210> SEQ ID NO 73
<211> LENGTH: 1527
<212> TYPE: DNA
<213> ORGANISM: Artificial Sequence
<220> FEATURE:
<223> OTHER INFORMATION: Synthesized

<400> SEQUENCE: 73
gagcccaaat cttgtgacaa aactcacaca tgcccaccgt gcccagcacc tgaactcctg 60
gggggaccgt cagtcttcct cttcccccca aaacccaagg acaccctcat gatctcccgg 120
acccctgagg tcacatgcgt ggtggtggac gtgagccacg aagaccctga ggtcaagttc 180
aactggtacg tggacggcgt ggaggtgcat aatgccaaga caaagccgcg ggaggagcag 240
tacaacagca cgtaccgtgt ggtcagcgtc ctcaccgtcc tgcaccagga ctggctgaat 300
ggcaaggagt acaagtgcaa ggtctccaac aaagccctcc cagcccccat cgagaaaacc 360
atctccaaag ccaaagggca gccccgagaa ccacaggtgt acaccctgcc cccatcccgg 420

```
gaggagatga ccaagaacca ggtcagcctg acctgcctgg tcaaaggctt ctatcccagc    480

gacatcgccg tggagtggga gagcaatggg cagccggaga acaactacaa gaccacgcct    540

cccgtgctgg actccgacgg ctccttcttc ctctatagca agctcaccgt ggacaagagc    600

aggtggcagc aggggaacgt cttctcatgc tccgtgatgc atgaggctct gcacaaccac    660

tacacgcaga agagcctctc cctgtctccg ggtaaaggcg gtggagggtc cggaggcggg    720

ggttccggcg gaggtggctc aggaggcgga gggtcagggg gaggtggctc cggcggtgga    780

ggatccggcg gtggtggatc agaggttcag ctggtggagt ctggcggtgg cctggtgcag    840

ccagggggct cactccgttt gtcctgtgca gcttctggct tcaacattaa agacacctat    900

atacactggg tgcgtcaggc cccgggtaag ggcctggaat gggttgcaag gatttatcct    960

acgaatggtt atactagata tgccgatagc gtcaagggcc gtttcactat aagcgcagac   1020

acatccaaaa acacagccta cctgcagatg aacagcctgc gtgctgagga cactgccgtc   1080

tattattgtt ctagatgggg aggggacggc ttctatgcta tggactactg gggtcaagga   1140

accctggtca ccgtctcctc gggtggaggc ggttcaggcg gaggtggttc cggcggtggc   1200

ggctccgata tccagatgac ccagtccccg agctccctgt ccgcctctgt gggcgatagg   1260

gtcaccatca cctgccgtgc cagtcaggat gtgaatactg ctgtagcctg gtatcaacag   1320

aaaccaggaa aagctccgaa actactgatt tactcggcat ccttcctcta ctctggagtc   1380

ccttctcgct tctctggctc cagatctggg acggatttca ctctgaccat cagcagtctg   1440

cagccggaag acttcgcaac ttattactgt cagcaacatt atactactcc tcccacgttc   1500

ggacagggta ccaaggtgga gatcaaa                                       1527
```

```
<210> SEQ ID NO 74
<211> LENGTH: 509
<212> TYPE: PRT
<213> ORGANISM: Artificial Sequence
<220> FEATURE:
<223> OTHER INFORMATION: Synthesized

<400> SEQUENCE: 74

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160
```

-continued

```
Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Gly Gly Gly Gly Ser Gly Gly Gly
225                 230                 235                 240

Gly Ser Gly Gly Gly Gly Ser Gly Gly Gly Gly Ser Gly Gly Gly Gly
                245                 250                 255

Ser Gly Gly Gly Gly Ser Gly Gly Gly Gly Ser Glu Val Gln Leu Val
            260                 265                 270

Glu Ser Gly Gly Gly Leu Val Gln Pro Gly Gly Ser Leu Arg Leu Ser
        275                 280                 285

Cys Ala Ala Ser Gly Phe Asn Ile Lys Asp Thr Tyr Ile His Trp Val
    290                 295                 300

Arg Gln Ala Pro Gly Lys Gly Leu Glu Trp Val Ala Arg Ile Tyr Pro
305                 310                 315                 320

Thr Asn Gly Tyr Thr Arg Tyr Ala Asp Ser Val Lys Gly Arg Phe Thr
                325                 330                 335

Ile Ser Ala Asp Thr Ser Lys Asn Thr Ala Tyr Leu Gln Met Asn Ser
            340                 345                 350

Leu Arg Ala Glu Asp Thr Ala Val Tyr Tyr Cys Ser Arg Trp Gly Gly
        355                 360                 365

Asp Gly Phe Tyr Ala Met Asp Tyr Trp Gly Gln Gly Thr Leu Val Thr
    370                 375                 380

Val Ser Ser Gly Gly Gly Gly Ser Gly Gly Gly Gly Ser Gly Gly Gly
385                 390                 395                 400

Gly Ser Asp Ile Gln Met Thr Gln Ser Pro Ser Ser Leu Ser Ala Ser
                405                 410                 415

Val Gly Asp Arg Val Thr Ile Thr Cys Arg Ala Ser Gln Asp Val Asn
            420                 425                 430

Thr Ala Val Ala Trp Tyr Gln Gln Lys Pro Gly Lys Ala Pro Lys Leu
        435                 440                 445

Leu Ile Tyr Ser Ala Ser Phe Leu Tyr Ser Gly Val Pro Ser Arg Phe
    450                 455                 460

Ser Gly Ser Arg Ser Gly Thr Asp Phe Thr Leu Thr Ile Ser Ser Leu
465                 470                 475                 480

Gln Pro Glu Asp Phe Ala Thr Tyr Tyr Cys Gln Gln His Tyr Thr Thr
                485                 490                 495

Pro Pro Thr Phe Gly Gln Gly Thr Lys Val Glu Ile Lys
            500                 505
```

<210> SEQ ID NO 75
<211> LENGTH: 242
<212> TYPE: PRT
<213> ORGANISM: Artificial Sequence
<220> FEATURE:
<223> OTHER INFORMATION: Synthesized

<400> SEQUENCE: 75

```
Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Asp Ile Gln Met Thr Gln Ser Pro Ser
130 135 140

Ser Leu Ser Ala Ser Val Gly Asp Arg Val Thr Ile Thr Cys Arg Ala
145 150 155 160

Ser Gln Asp Val Asn Thr Ala Val Ala Trp Tyr Gln Gln Lys Pro Gly
165 170 175

Lys Ala Pro Lys Leu Leu Ile Tyr Ser Ala Ser Phe Leu Tyr Ser Gly
180 185 190

Val Pro Ser Arg Phe Ser Gly Ser Arg Ser Gly Thr Asp Phe Thr Leu
195 200 205

Thr Ile Ser Ser Leu Gln Pro Glu Asp Phe Ala Thr Tyr Tyr Cys Gln
210 215 220

Gln His Tyr Thr Thr Pro Pro Thr Phe Gly Gln Gly Thr Lys Val Glu
225 230 235 240

Ile Lys

<210> SEQ ID NO 76
<211> LENGTH: 1542
<212> TYPE: DNA
<213> ORGANISM: Artificial Sequence
<220> FEATURE:
<223> OTHER INFORMATION: Synthesized

<400> SEQUENCE: 76
gagcccaaat cttgtgacaa aactcacaca tgcccaccgt gcccagcacc tgaactcctg 60
gggggaccgt cagtcttcct cttcccccca aaacccaagg acaccctcat gatctcccgg 120
acccctgagg tcacatgcgt ggtggtggac gtgagccacg aagaccctga ggtcaagttc 180
aactggtacg tggacggcgt ggaggtgcat aatgccaaga caaagccgcg ggaggagcag 240
tacaacagca cgtaccgtgt ggtcagcgtc ctcaccgtcc tgcaccagga ctggctgaat 300
ggcaaggagt acaagtgcaa ggtctccaac aaagccctcc cagcccccat cgagaaaacc 360
atctccaaag ccaaagggca gccccgagaa ccacaggtgt acaccctgcc cccatcccgg 420
gaggagatga ccaagaacca ggtcagcctg acctgcctgg tcaaaggctt ctatcccagc 480
gacatcgccg tggagtggga gagcaatggg cagccggaga acaactacaa gaccacgcct 540
cccgtgctgg actccgacgg ctccttcttc ctctatagca agctcaccgt ggacaagagc 600
aggtggcagc aggggaacgt cttctcatgc tccgtgatgc atgaggctct gcacaaccac 660
tacacgcaga agagcctctc cctgtctccg ggtaaagggg gaggtggctc cggcggtgga 720
gggtccggag gcgggggttc cggcggaggt ggctcaggag gcggagggtc agggggaggt 780

```
ggctccggcg gtggaggatc cggcggtggt ggatcagagg ttcagctggt ggagtctggc    840

ggtggcctgg tgcagccagg gggctcactc cgtttgtcct gtgcagcttc tggcttcaac    900

attaaagaca cctatataca ctgggtgcgt caggccccgg gtaagggcct ggaatgggtt    960

gcaaggattt atcctacgaa tggttatact agatatgccg atagcgtcaa gggccgtttc   1020

actataagcg cagacacatc caaaaacaca gcctacctgc agatgaacag cctgcgtgct   1080

gaggacactg ccgtctatta ttgttctaga tggggagggg acggcttcta tgctatggac   1140

tactggggtc aaggaaccct ggtcaccgtc tcctcgggtg gaggcggttc aggcggaggt   1200

ggttccggcg gtggcggctc cgatatccag atgacccagt ccccgagctc cctgtccgcc   1260

tctgtgggcg atagggtcac catcacctgc cgtgccagtc aggatgtgaa tactgctgta   1320

gcctggtatc aacagaaacc aggaaaagct ccgaaactac tgatttactc ggcatccttc   1380

ctctactctg gagtcccttc tcgcttctct ggctccagat ctgggacgga tttcactctg   1440

accatcagca gtctgcagcc ggaagacttc gcaacttatt actgtcagca acattatact   1500

actcctccca cgttcggaca gggtaccaag gtggagatca aa                      1542
```

<210> SEQ ID NO 77
<211> LENGTH: 514
<212> TYPE: PRT
<213> ORGANISM: Artificial Sequence
<220> FEATURE:
<223> OTHER INFORMATION: Synthesized

<400> SEQUENCE: 77

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220
```

```
Ser Leu Ser Leu Ser Pro Gly Lys Gly Gly Gly Gly Ser Gly Gly Gly
225                 230                 235                 240

Gly Ser Gly Gly Gly Gly Ser Gly Gly Gly Gly Ser Gly Gly Gly Gly
                245                 250                 255

Ser Gly Gly Gly Gly Ser Gly Gly Gly Gly Ser Gly Gly Gly Gly Ser
            260                 265                 270

Glu Val Gln Leu Val Glu Ser Gly Gly Gly Leu Val Gln Pro Gly Gly
        275                 280                 285

Ser Leu Arg Leu Ser Cys Ala Ala Ser Gly Phe Asn Ile Lys Asp Thr
    290                 295                 300

Tyr Ile His Trp Val Arg Gln Ala Pro Gly Lys Gly Leu Glu Trp Val
305                 310                 315                 320

Ala Arg Ile Tyr Pro Thr Asn Gly Tyr Thr Arg Tyr Ala Asp Ser Val
                325                 330                 335

Lys Gly Arg Phe Thr Ile Ser Ala Asp Thr Ser Lys Asn Thr Ala Tyr
            340                 345                 350

Leu Gln Met Asn Ser Leu Arg Ala Glu Asp Thr Ala Val Tyr Tyr Cys
        355                 360                 365

Ser Arg Trp Gly Gly Asp Gly Phe Tyr Ala Met Asp Tyr Trp Gly Gln
    370                 375                 380

Gly Thr Leu Val Thr Val Ser Ser Gly Gly Gly Gly Ser Gly Gly Gly
385                 390                 395                 400

Gly Ser Gly Gly Gly Gly Ser Asp Ile Gln Met Thr Gln Ser Pro Ser
                405                 410                 415

Ser Leu Ser Ala Ser Val Gly Asp Arg Val Thr Ile Thr Cys Arg Ala
            420                 425                 430

Ser Gln Asp Val Asn Thr Ala Val Ala Trp Tyr Gln Gln Lys Pro Gly
        435                 440                 445

Lys Ala Pro Lys Leu Leu Ile Tyr Ser Ala Ser Phe Leu Tyr Ser Gly
    450                 455                 460

Val Pro Ser Arg Phe Ser Gly Ser Arg Ser Gly Thr Asp Phe Thr Leu
465                 470                 475                 480

Thr Ile Ser Ser Leu Gln Pro Glu Asp Phe Ala Thr Tyr Tyr Cys Gln
                485                 490                 495

Gln His Tyr Thr Thr Pro Pro Thr Phe Gly Gln Gly Thr Lys Val Glu
            500                 505                 510

Ile Lys
```

<210> SEQ ID NO 78
<211> LENGTH: 242
<212> TYPE: PRT
<213> ORGANISM: Artificial Sequence
<220> FEATURE:
<223> OTHER INFORMATION: Synthesized

<400> SEQUENCE: 78

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
```

```
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln His Tyr Thr Thr Pro Pro Thr Phe Gly Gln Gly Thr Lys Val Glu
225                 230                 235                 240

Ile Lys


<210> SEQ ID NO 79
<211> LENGTH: 119
<212> TYPE: PRT
<213> ORGANISM: Artificial Sequence
<220> FEATURE:
<223> OTHER INFORMATION: Synthesized

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115


<210> SEQ ID NO 80
<211> LENGTH: 242
<212> TYPE: PRT
<213> ORGANISM: Artificial Sequence
<220> FEATURE:
<223> OTHER INFORMATION: Synthesized

<400> SEQUENCE: 80

Glu Val Gln Leu Val Glu Ser Gly Gly Gly Leu Val Gln Pro Gly Gly
```

-continued

```
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
            165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln His Tyr Thr Thr Pro Pro Thr Phe Gly Gln Gly Thr Lys Val Glu
225                 230                 235                 240

Ile Lys


<210> SEQ ID NO 81
<211> LENGTH: 5
<212> TYPE: PRT
<213> ORGANISM: Artificial Sequence
<220> FEATURE:
<223> OTHER INFORMATION: Synthesized

<400> SEQUENCE: 81

Gly Gly Gly Gly Ser
1               5
```

BISPECIFIC TETRAVALENT ANTIBODIES AND METHODS OF MAKING AND USING THEREOF

CROSS REFERENCE TO RELATED PATENT APPLICATIONS

This application is a national stage application of International Application No. PCT/US15/66952, filed Dec. 19, 2015, titled "bispecific tetravalent antibodies and methods of making and using thereof," which claims priority over U.S. Provisional Application No. 62/095,348, filed Dec. 22, 2014, titled "BISPECIFIC ANTIBODIES," which is hereby incorporated by reference in its entirety.

SEQUENCE LISTING

The Sequence Listing associated with this application is provided in text format in lieu of a paper copy, and is hereby incorporated by reference into the specification. The name of the text file containing the Sequence Listing is Sequence Listing_ST25_0003PCT2.txt. The text file is about 164 KB, was created on Dec. 18, 2015, and is being submitted electronically via EFS-Web.

TECHNICAL FIELD

The present disclosure generally relates to the technical field of antibodies, and more particularly relates to bispecific antibodies.

BACKGROUND

HER2, a member of the ErbB/HER receptor family, is overexpressed and/or deregulated in several cancers of the breast and ovary (King, Kraus and Aaronson, *Science* 1985; 229: 974-976; Slamon et al., *Science* 1989; 244:707-712). Therapeutics targeting HER2 have been used successfully in the clinic and have been approved by the US FDA. Such antibody therapeutics includes trastuzumab (Horton, *Cancer Control* 2001: 8(1), 103-110) and pertuzumab (Badache and Hynes, *Cancer Cell;* 5(4): 299-301). Several studies have indicated that therapeutic enhancement may be achieved by combining two or more epitope-distinct anti-HER2 antibodies such as trastuzumab and pertuzumab compared to a single antibody monotherapy (Kasprzyk et al., *Cancer Res* 1992; 52: 2771-2776, Ben-Kasus et al., *Proc Natl Acad Sci USA,* 106(9) 3294-3329). Trastuzumab which binds to the extracellular domain 4 of HER2 inhibits ligand independent signaling, stimulates ADCC, blocks HER2 shedding but does not inhibit HER2 dimerization. Pertuzumab which binds to the extracellular domain 2 inhibits HER2 dimerization and dimerization with other HER family receptors, inhibits multiple ligand-dependent HER mediated signaling pathways and stimulates ADCC (O'Sullivan and Connolly, *Oncology* 2014; 28(3): 186-194).

A combination of Pertuzumab and Trastuzumab for the treatment of HER2-positive metastatic cancer has been approved by FDA in 2013 as a new treatment for HER2-positive breast cancer, based on substantial clinical benefit seen over Trastuzumab alone (Baselga et al. *N Engl J Med.* 2012 Jan. 12; 366(2):109-19). However, the efficacy of the use of the simple combination of two or more monoclonal antibodies is sub-optimal. In addition, the cost of producing two or more monoclonal antibodies separately is high.

Therefore, there is a need to improve the efficacy of cancer treatment by combining monoclonal antibodies and reduce the cost associated with the monoclonal antibody productions.

SUMMARY

The disclosure provides bispecific tetravalent antibodies. The bispecific tetravalent antibody may include two IgG1 heavy chains; two kappa light chains; and two single chain Fv (scFv) domains. The two IgG1 heavy chains and kappa light chains may form an IgG moiety with a binding specificity to a first domain of HER2. The two scFv domains may have a binding specificity to a second domain of HER2. The IgG moiety and two scFv domains are covalently connected to be functional as a bispecific tetravalent antibody. The objectives and advantages of the disclosure may become apparent from the following detailed description of preferred embodiments thereof in connection with the accompanying drawings.

BRIEF DESCRIPTION OF THE DRAWINGS

Preferred embodiments according to the present disclosure may now be described with reference to the FIGs, in which like reference numerals denote like elements.

DETAILED DESCRIPTION

Figure 1:
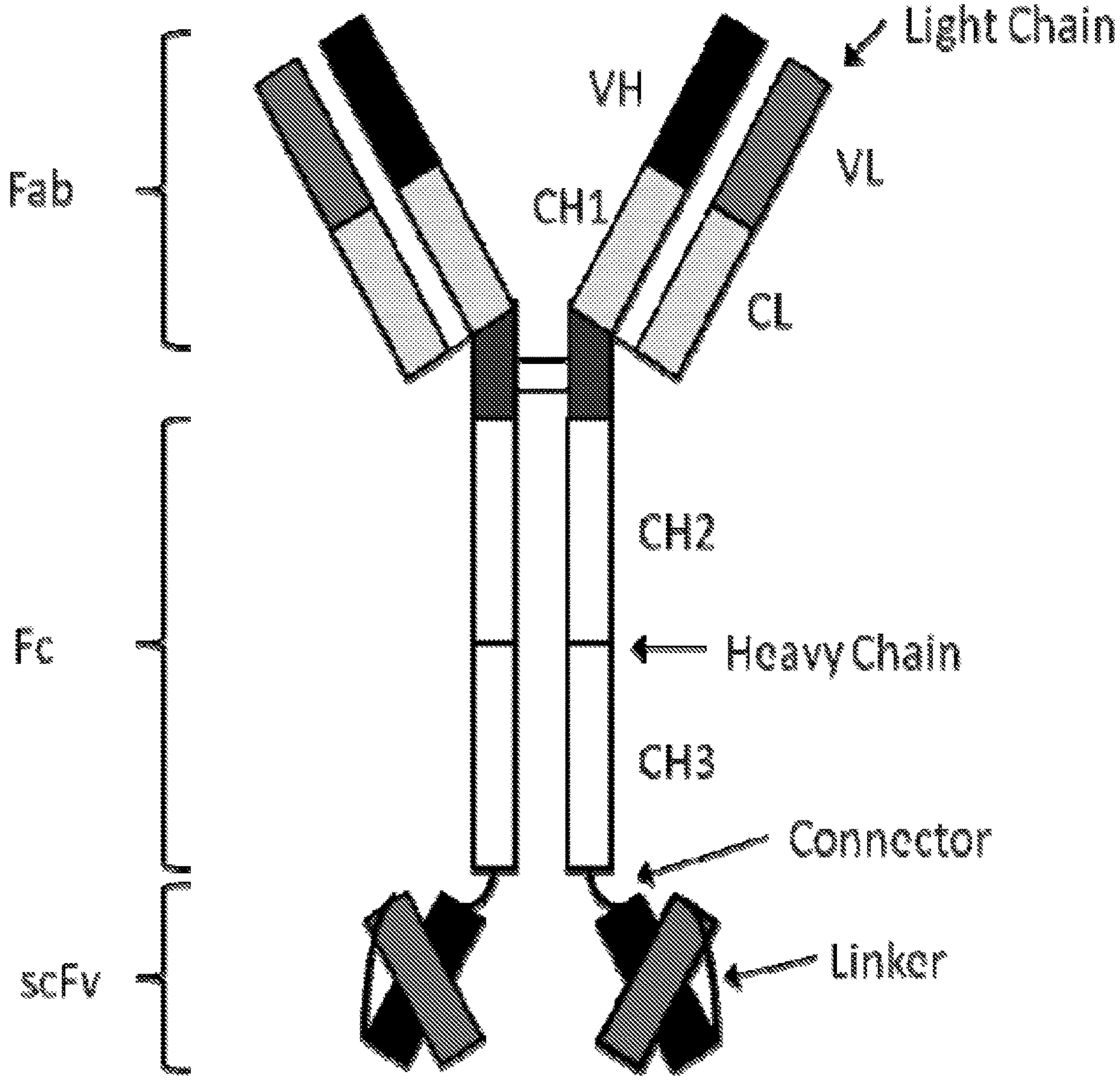
FIG. 1 shows the tetravalent bispecific antibody structure in accordance with one embodiment of the present invention.

This disclosure provides bispecific tetravalent antibodies. The antibodies may have advantage of targeting both extracellular domains 2 and 4 of HER2 simultaneously.

It must be noted that as used herein and in the appended claims, the singular forms "a", "and", and "the" in Throughout this specification and claims, the word "comprise," or variations such as "comprises" or "comprising," will be understood to imply the inclusion of a stated integer or group of integers but not the exclusion of any other integer or group of integers include plural referents unless the context clearly dictates otherwise.

"Antibody fragments" comprise a portion of an intact antibody, preferably the antigen-binding or variable region of the intact antibody. Examples of antibody fragments include Fv, Fab, Fab', F(ab')2, Fab'-SH; diabodies; linear antibodies (see U.S. Pat. No. 5,641,870, Example 2; Zapata et al., Protein Eng. 8(10): 1057-1062 (1995)); single-chain antibody molecules (e.g. scFv). While in the present description, and throughout the specification, reference is made to antibodies and various properties of antibodies, the same disclosure also applies to functional antibody fragments, e.g. dual action Fab fragments.

In one aspect, the bispecific tetravalent antibody may include two IgG1 heavy chains; two kappa light chains; and two single chain Fv (scFv) domains. The two IgG1 heavy chains and kappa light chains may form an IgG moiety with a binding specificity to a first domain of HER2. The two scFv domains may have a binding specificity to a second domain of HER2. Each scFv domain may be connected to the C-terminal residue of either of the IgG1 heavy chains by a connector having an amino acid sequence of (gly-gly-gly-gly-ser)$_n$(($G_4S$)$_n$). Each scFv domain may have a structure order of N terminus-variable heavy-linker-variable light-C terminus or N-terminus-variable light-linker-variable heavy-C-terminus, and the linker may include an amino acid sequence of (gly-gly-gly-gly-ser)$_m$ (($G_4S$)$_m$). Both n and m are integrals. n may be an integral of at least 2. In one embodiment, n is from 1 to 10 or 2 to 9. In some embodiments, n is at least 9. In some embodiments, n is from 2 to 20. m may be an integral of at least 2. In some embodiment, m may be 2, 3, 4, or 5. In some embodiments, m may an integral selected from 2, 3, 4, 5, 6, 7, 8, 9, and 10.

In some embodiments, at least one of the IgG1 heavy chains or the kappa light chains is humanized or human. In some embodiments, both IgG1 heavy chains are humanized or human. In some embodiments, both kappa light chains are humanized or human.

In some embodiments, the domain of HER2 is independently selected from domain 2 and domain 4 of HER2. In some embodiments, the bispecific tetravalent antibody may include an IgG moiety with scFv connecting to either C or N terminals of heave or light chains via a peptide linker. The IgG moiety may have binding specificity to extracellular domain 2 or 4 of HER2 (human epidermal growth factor 2) expressing cells while the scFv domains may have binding specificity to ectodomain 4 or 2 of HER2 expressing cells, respectively. The binding may be bivalent.

The peptide linker may vary in length. In some embodiments, the peptide linker may include from about 15 to about 45 amino acids. In some embodiments, the peptide linkers may include from about 20 to about 50 amino acids. In some embodiments, the peptide linkers may include from about 10 to about 30 amino acids.

In some embodiments, the IgG moiety may have a binding specificity for domain 2 of HER2. In some embodiments, the scFv domains may have a binding specificity for domain 4 of HER2. In some embodiments, the IgG moiety may have a binding specificity for domain 4 of HER2. In some embodiments, the scFv domains may have a binding specificity for domain 2 of HER2.

In some embodiments, at least one of or both the IgG1 heavy chains comprises an amino acid sequences of or with at least 95%, 98%, or 99% similarity to SEQ ID NO 7, 15, 30, 40, 50 and 58. In some embodiments, the IgG1 heavy chain, connector, and scFv domain have an amino acid sequence of or with at least 95%, 98%, or 99% similarity to SEQ ID NO 30, 50, 40, and 58. In some embodiments, at least one of or both the kappa light chains comprises an amino acid sequence of or with at least 95%, 98%, or 99% similarity to SEQ ID NO 3, 11, 25, 35, 45, and 53. In some embodiments, at least one of or both variable light chain comprises an amino acid sequence of or with at least 95%, 98%, or 99% similarity to SEQ ID NO 4, 12, 26, 36, 46, and 54. In some embodiments, at least one of or both variable heavy chain comprises an amino acid sequence of or with at least 95%, 98%, or 99% similarity to SEQ ID NO 8, 16, 31, 41, 79 and 59. In some embodiments, at least one of or both scFv domain comprises an amino acid sequence of or with at least 95%, 98%, or 99% similarity to SEQ ID NO 19, 22, 32, 42, 80, 60, 63, 66, 69, 72, 75, 78.

In some embodiments, the IgG moiety may have a binding specificity for domain 2 of HER2, and the scFv domains may have a binding specificity for domain 4 of HER2. In one embodiment, the IgG1 heavy chain, connector, and scFv domain may have an amino acid sequence of or with at least 95% similarity to SEQ ID NO 30, and the kappa light chain may have an amino acid sequence of or with at least 95% similarity to SEQ ID NO 25. In one embodiment, the IgG1 heavy chain, connector, and scFv domain may have an amino acid sequence of or with at least 95% similarity to SEQ ID NO 50, and the kappa light chain may have an amino acid sequence of or with at least 95% similarity to SEQ ID NO 45.

In some embodiments, the IgG moiety may have a binding specificity for domain 4 of HER2, and the scFv domains may have a binding specificity for domain 2 of HER2. In one embodiment, the IgG1 heavy chain, connector, and scFv domain may have an amino acid sequence of or with at least 95% similarity to SEQ ID NO 40, and the kappa light chain has an amino acid sequence of or with at least 95% similarity to SEQ ID NO 35. In one embodiment, the IgG1 heavy chain, connector, and scFv domain may have an amino acid sequence of or with at least 95% similarity to SEQ ID NO 58, and the kappa light chain may have an amino acid sequence of or with at least 95% similarity to SEQ ID NO 53.

The bispecific tetravalent antibodies have the activity of inhibiting cancer cell growth. In certain embodiments, an antibody of the invention has a dissociation constant (Kd) of ≤80 nM, ≤50 nM, ≤30 nM, ≤20 nM, 1510 nM, or nM for its target EGRF or HER3. The antibody may bind to both targets simultaneously. In some embodiments, the antibody may bind to domain 2 of HER2 with a Kd less than 1 nM, 10 nM, 20 nM, ≤0 nM, or 100 nM. In some embodiments, the antibody may bind to domain 4 of HER2 with a Kd less than 5 nM, 10 nM, 20 nM, ≤0 nM, or 100 nM. In some embodiments, the antibody may bind to domain 4 of HER2 with a Kd less than 30 nM and binds to domain 2 of HER2 with a Kd less than 30 nM. In some embodiments, the antibody may bind to domain 4 of HER2 with a Kd less than 50 nM and binds to domain 2 of HER2 with a Kd less than 20 nM simultaneously.

In some embodiments, the IgG moiety may provide stability to the scFv domains. In addition and alternatively, the IgG moiety may provide specificity to the epitope. In some embodiments, the bispecific antibody may mediate ADCC (antibody dependent cell-mediated cytotoxicity) towards cells expressing HER2. In some embodiments, the antibody may be capable of binding at least two domains (i.e. epitopes) on the HER2 antigen. In some embodiments, the antibody may bind multiple domains on the HER2 antigen simultaneously.

In some embodiments, the antibody may provide stronger tumour inhibition in proliferation assays in vitro and in vivo than the mono-specific antibody parental controls or combination of mono-specific antibody parental controls. Not wanting to be bound by theory, it is believed that, by acting against the same antigen of two different epitopes, the bispecific tetravalent antibody disclosed herein may enhance internalization of the receptor (HER2) and down regulate the signalling pathway more efficiently than each of the individual mono-specific antibody or combination of the two mono-specific antibodies.

In some embodiments, the bispecific tetravalent antibody may inhibit a cancer cell growth. In some embodiments, the cancer cell may express HER2. In some embodiments, the bispecific tetravalent antibody may inhibit a cancer cell growth. In some embodiments, the cancer cell may express HER2+.

In another aspect, the disclosure provides isolated nucleic acids encoding the bispecific tetravalent antibodies, a fragment or a subcomponent disclosed herein.

In a further aspect, the disclosure provides expression vectors having the isolated nucleic acids encoding the bispecific tetravalent antibody, a fragment or a subcomponent disclosed herein. The vectors may be expressible in a host cell. The host cell may be prokaryotic or eukaryotic.

In a further aspect, the disclosure provides host cells having the isolated nucleic acids encoding the bispecific tetravalent antibody, a fragment or a subcomponent disclosed herein or the expression vectors including such nucleic acid sequences.

In a further aspect, the disclosure provides methods for producing bispecific tetravalent antibodies. In one embodiment, the method may include culturing the above-described host cells so that the antibody is produced.

In a further aspect, the disclosure provides immunoconjugates including the bispecific tetravalent antibodies described herein and a cytotoxic agent.

In a further aspect, the disclosure provides pharmaceutical compositions. The pharmaceutical composition may include the bispecific tetravalent antibodies or the immunoconjugates described herein and a pharmaceutically acceptable carrier. In some embodiments, the composition may further include radioisotope, radionuclide, a toxin, a therapeutic agent, a chemotherapeutic agent or a combination thereof.

In a further aspect, the disclosure provides methods of treating a subject with a cancer. In one embodiment, the method includes the step of administering to the subject an effective amount of a bispecific tetravalent antibody described herein. The cancer may include cells expressing HER2, a domain, an epitope, a fragment or a derivative thereof. The cancer may be HER2+ breast cancer, colorectal cancer, ovarian cancer, gastric cancer, esophageal cancer, head and neck cancer and non small cell lung cancer.

In one embodiment, the method may further include co-administering an effective amount of a therapeutic agent. The therapeutic agent may be, for example, an antibody, a chemotherapy agent, an enzyme, or a combination thereof. In some embodiments, the therapeutic agent may be an anti-estrogen agent, a receptor tyrosine inhibitor, or a combination thereof. In some embodiments, the therapeutic agent may be capecitabine, cisplatin, trastuzumab, fulvestrant, tamoxifen, letrozole, exemestane, anastrozole, aminoglutethimide, testolactone, vorozole, formestane, fadrozole, letrozole, erlotinib, lafatinib, dasatinib, gefitinib, imatinib, pazopinib, lapatinib, sunitinib, nilotinib, sorafenib, nabpalitaxel. In some embodiments, the subject in need of such treatment is a human. In some embodiments, the therapeutic agent may be a biologics. In some embodiments, the therapeutic agent may be a checkpoint inhibitor including but not limited to PD1, PDL1, CTLA4, 4-1BB, 0X40, GITR, TIM3, LAGS, TIGIT, CD40, CD27, HVEM, BTLA, VISTA, and B7H4.

In one embodiment, the disclosure provides methods for treating a subject by administering to the subject an effective amount of the bispecific tetravalent antibody to inhibit a biological activity of a HER2 receptor.

In one embodiment, the disclosure provides solutions having an effective concentration of the bispecific tetravalent antibody. In one embodiment, the solution is blood plasma in a subject.

Figure 2A:
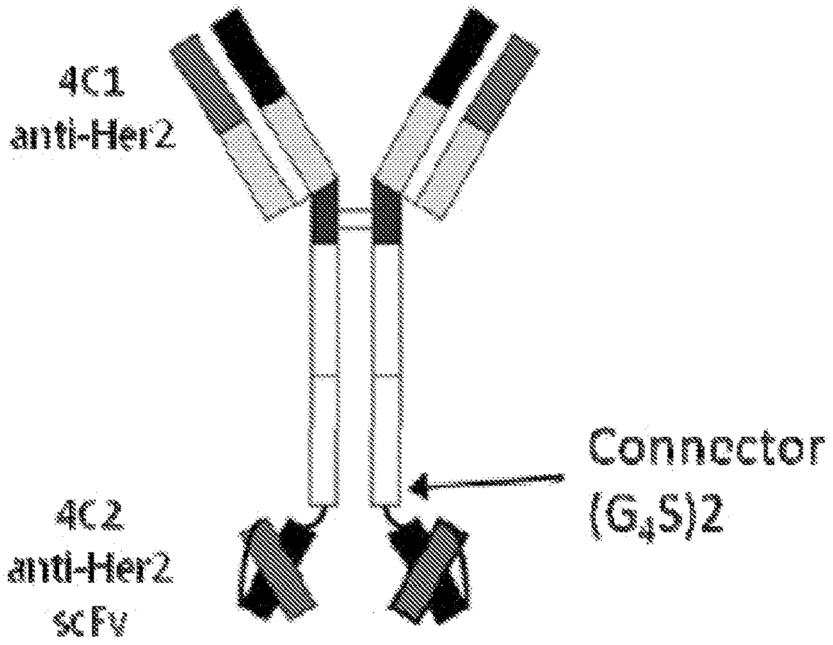
FIG. 2 shows the functional block diagrams of example tetravalent bispecific antibodies 4X1, 4X2, 4X3 and 4X4 in accordance with embodiments of the present invention.
Figure 2A:
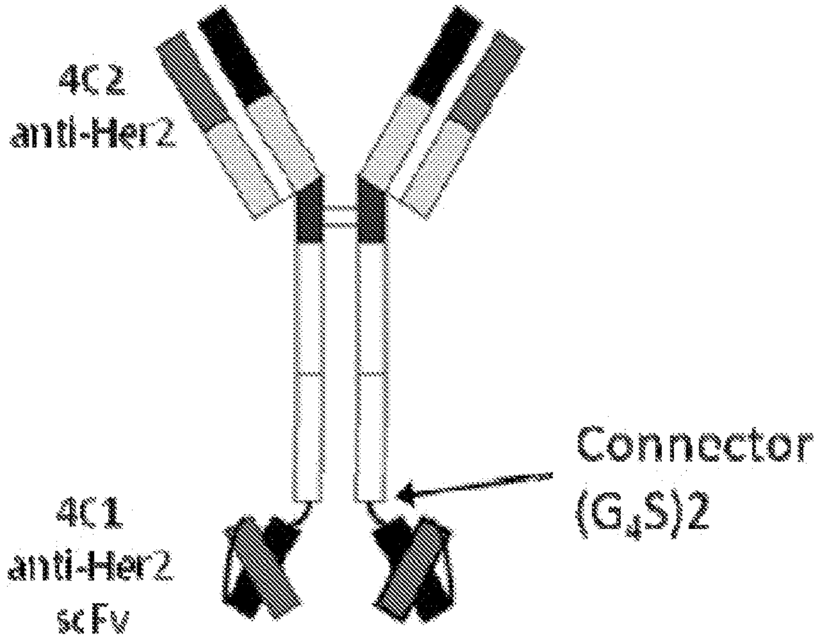
Figure 2B:
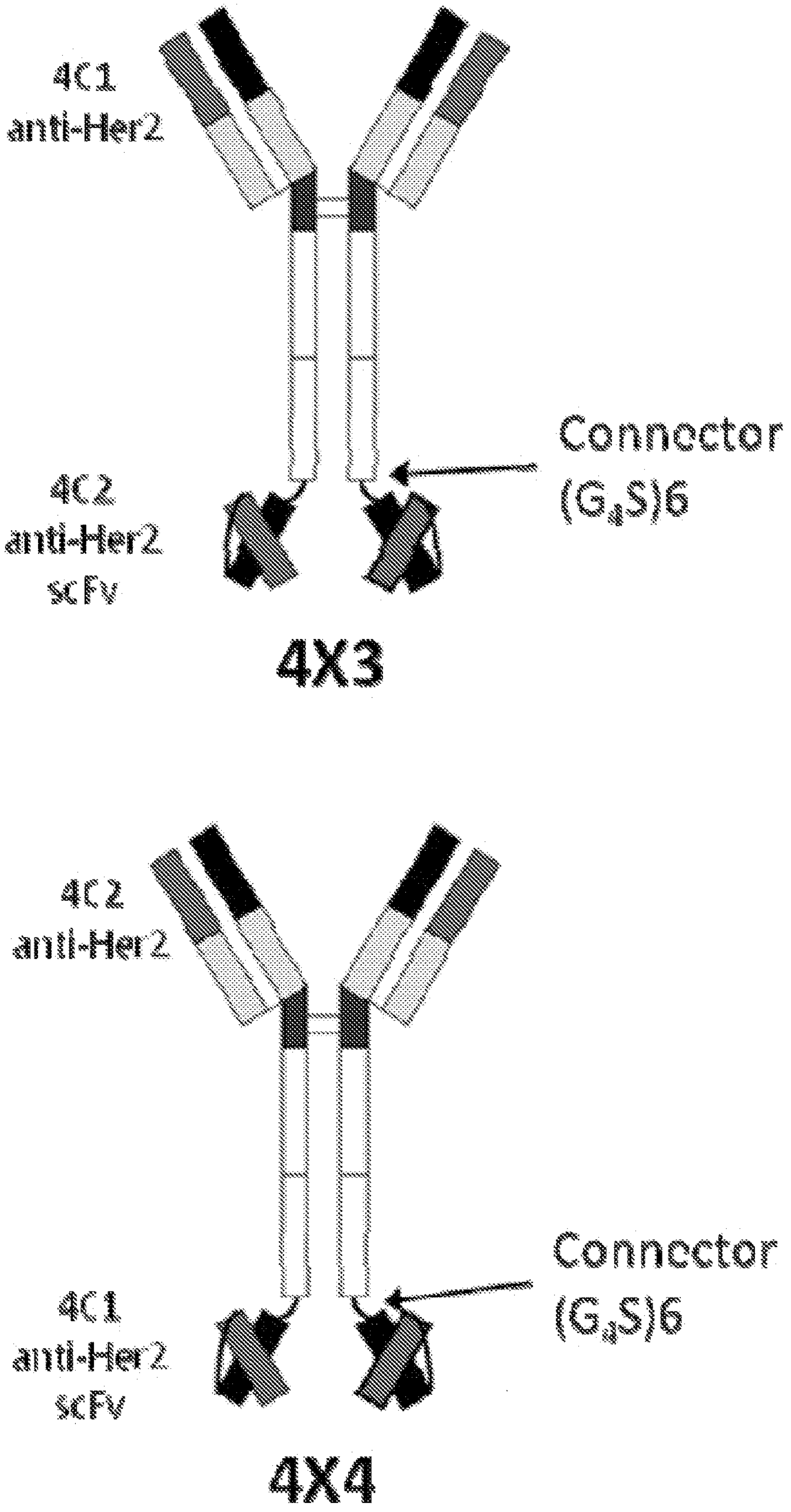
Figure 3:
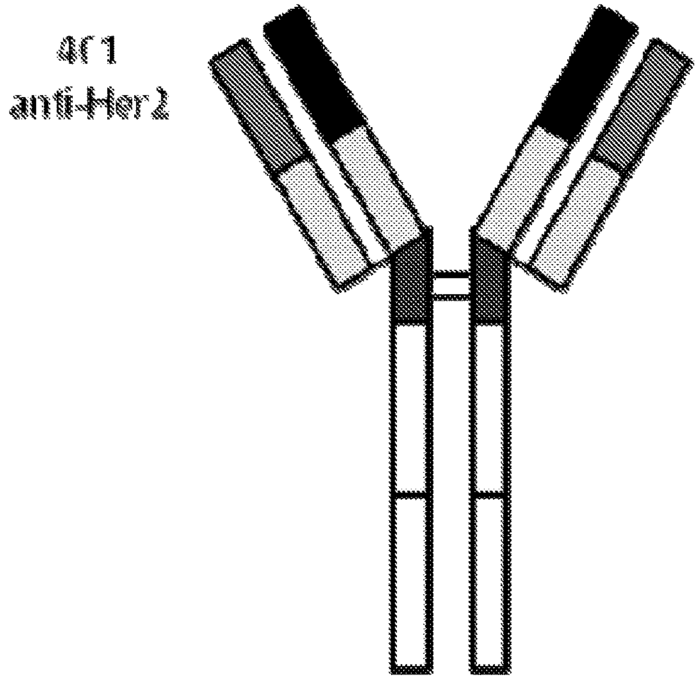
FIG. 3 shows the functional block diagram of example monospecific antibodies, 4C1 and 4C2
Figure 3:
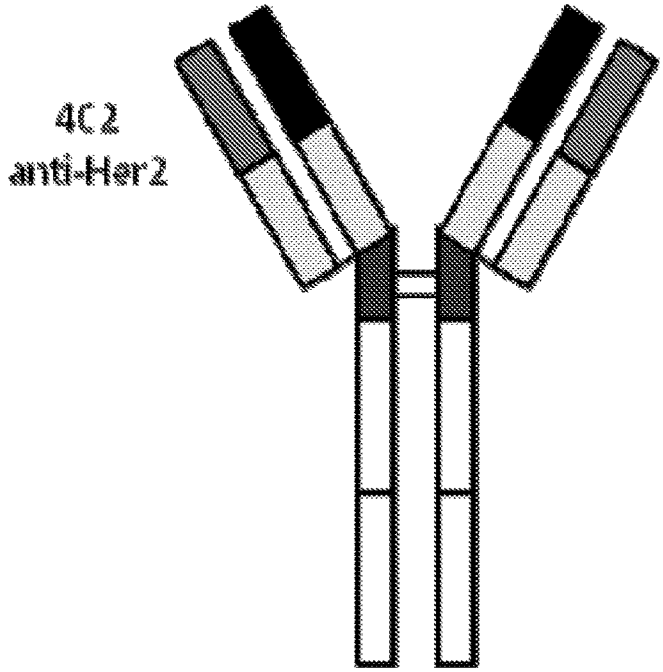
Figure 4A:
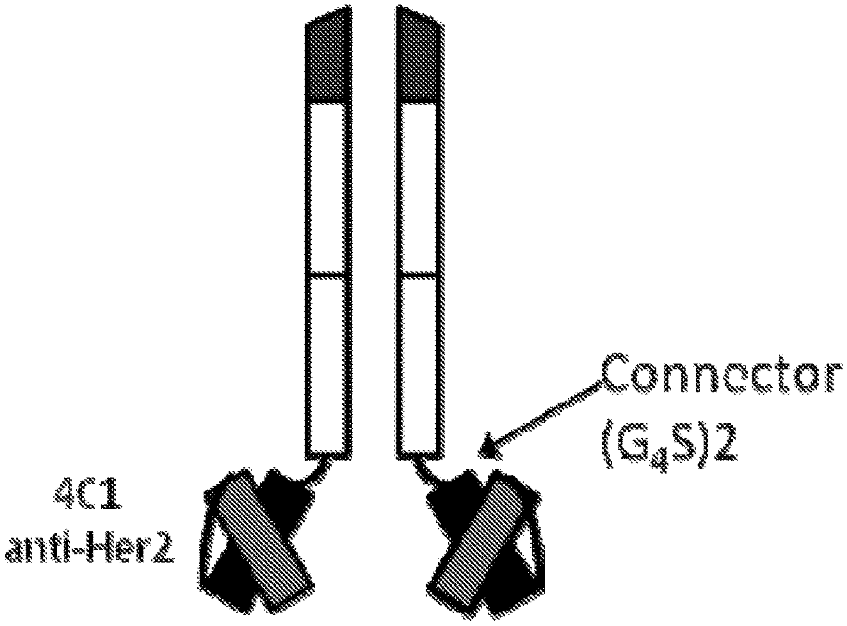
FIG. 4 shows the functional block diagram of example Fc-scFv antibodies 4C3, 4C4, 4C5, 4C6, 4C7, 4C8, 4C10 and 40.1.
Figure 4A:
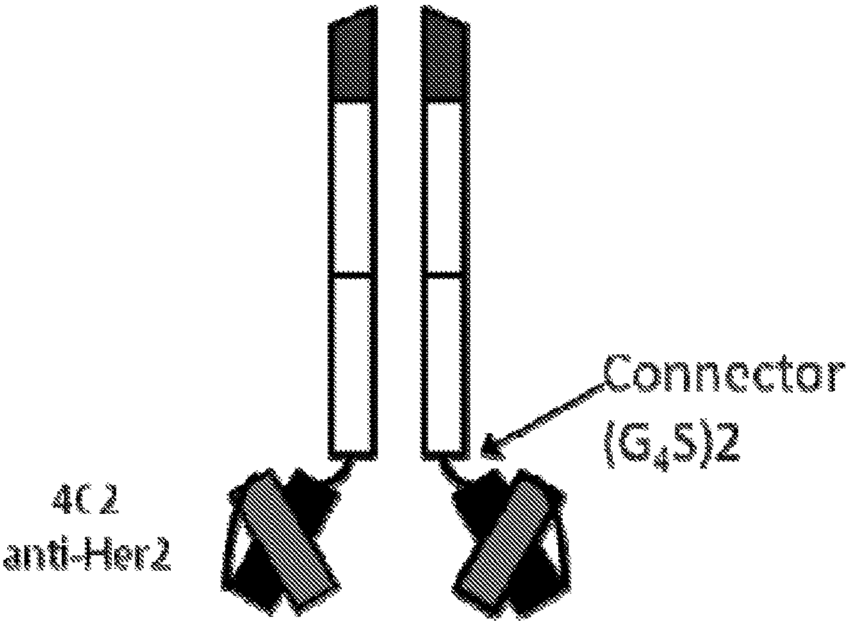
Figure 4B:
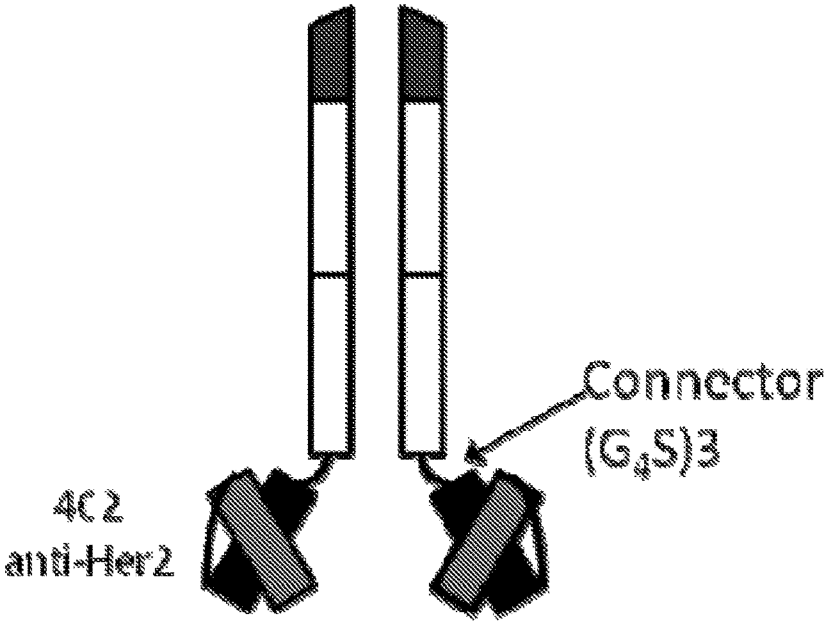
Figure 4B:
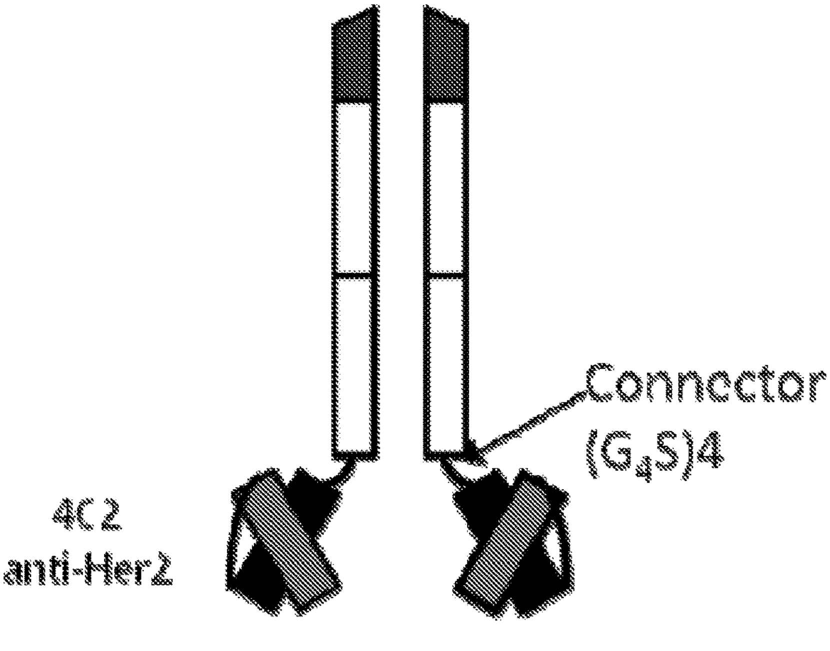
Figure 4C:
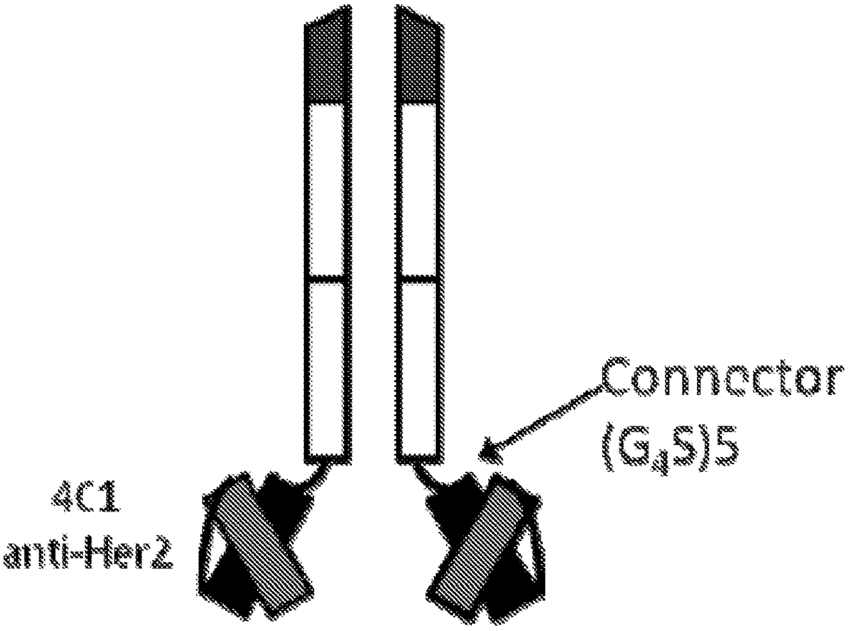
Figure 4C:
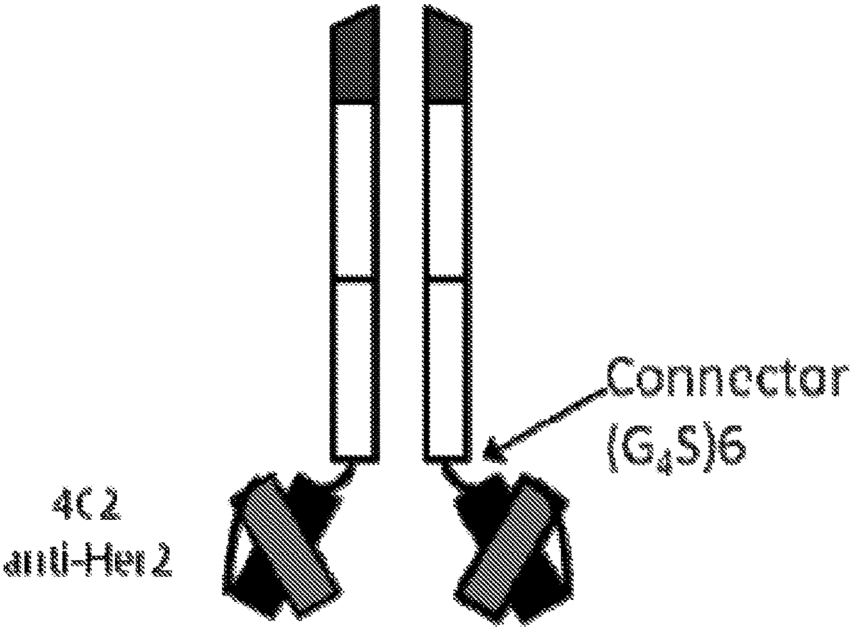
Figure 4D:
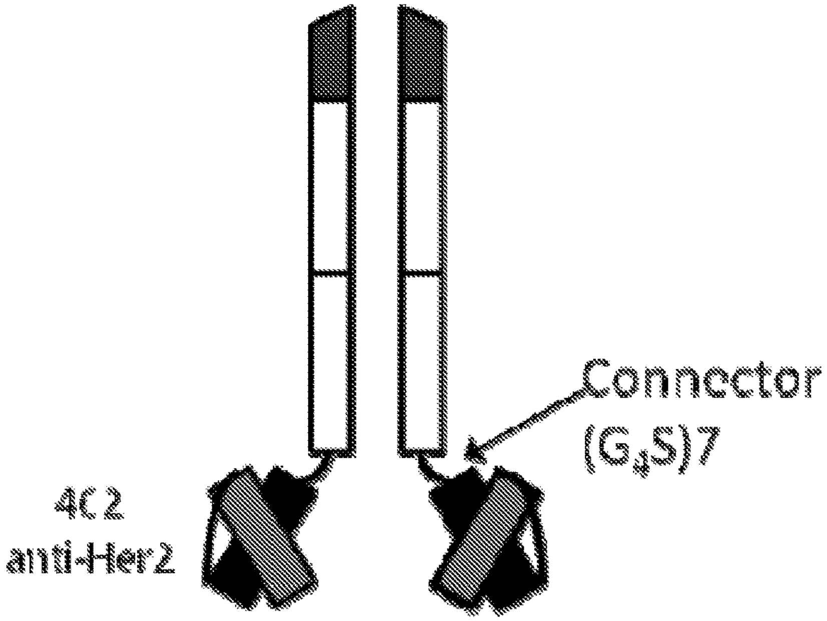
Figure 4D:
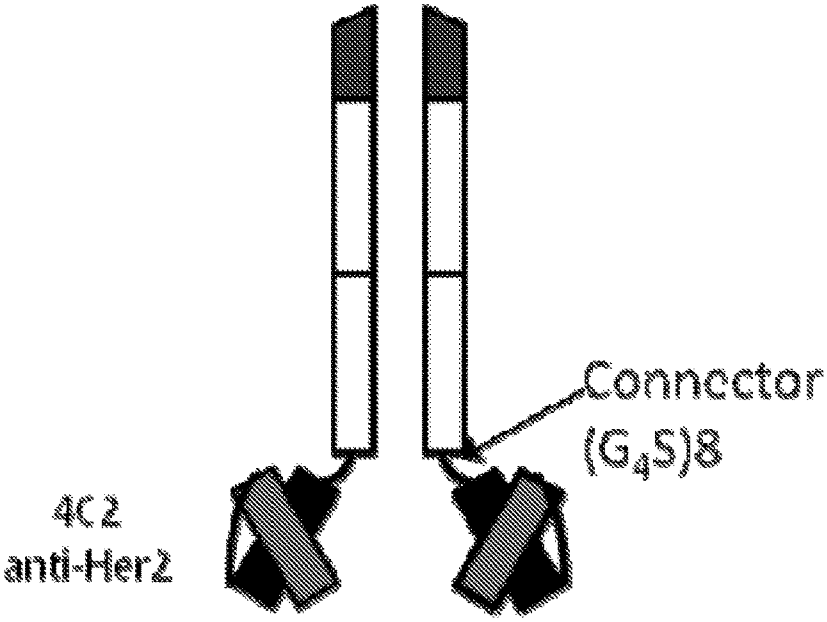

A diagram of the general structure of the bispecific tetravalent antibodies is shown in FIG. 1. In one embodiment, the bispecific tetravalent antibody includes two human IgG1 heavy chains, two human kappa light chain, and two single chain Fv (scFv) domains. The two human IgG1 heavy chains and human kappa light chains form an IgG moiety. The two scFv domains are respectively connected to the C-terminal residue of human IgG1 heavy chains with a connector with an amino acid sequence of repeats of gly-gly-gly-gly-ser- also known as $(G_4S)_n$, n can be integral. In one embodiment, n is from 2 to 10. In some embodiments, n may be from 1 to 15. The scFv may be in the order: N terminus-variable heavy-linker-variable light-C terminus. The scFv linker may include amino acid sequence of repeat of gly-gly-gly-gly-ser, also known as $(G_4S)_m$. m is an integral. For example, m may be 3 or 4. For all of the constructs, CH1, CH2, CH3 and CL amino acid sequences may be identical. There are 4 bispecific antibodies designated 4X1, 4X2, 4X3 and 4X4. These are depicted in FIG. 2.

Each bispecific tetravalent antibody may bind specifically to extracellular domain 2 of HER2 on one end and to extracellular domain 4 of HER2 on the other end. These 2 anti-HER2 binding domains are termed 4C1 and 4C2 respectively. Structure 4X1 has the 4C1 binding domain at the amino terminal end of the bispecific antibody in a conventional IgG1/kappa heavy and light chain format, with 4C2 added at the carboxyl terminal end as a single chain Fv. 4X2 is in the opposite orientation with 4C2 located at amino terminal end and 4C1 as the carboxyl terminal single chain Fv. There are a variety of additional types of bispecific antibody structures that could be created using these binding pairs, including changes to the linker and connector sequences and alternate location and/or format of these binding domains. For example, 4X3 can be created by extending the connector of 4X1 from $(G_4S)x2$ to $(G_4S)x6$ and 4X4 can be created by extending the connector of 4X2 from $(G_4S)x2$ to $(G_4S)x6$.

To study the effect of the length of the connecter, multiple Fc-scFv constructs designated 4C3, 4C4, 4C5, 4C6, 4C7, 4C8, 4C10 and 4C11 have been generated. 4C3 contained scFv from 4C1 whereas 4C4 contained scFv from 4C2. Connector variants from $(G_4S)x3$ to $(G_4S)x8$ were generated for 4C4 and shown on FIG. 4 for example, 4C5 has connector length of 15 amino acids $(G_4S)x3$ whereas 4C11 has connector length of 40 amino acids $(G_4S)x8$. TABLE 1 shows the connector length for different variants.

TABLE 1

Variant designation and connector lengths

| Variant Name | Connector length |
|---|---|
| 4C4 | $(G_4S) \times 2$ |
| 4C5 | $(G_4S) \times 3$ |
| 4C6 | $(G_4S) \times 4$ |
| 4C7 | $(G_4S) \times 5$ |
| 4C8 | $(G_4S) \times 6$ |
| 4C10 | $(G_4S) \times 7$ |
| 4C11 | $(G_4S) \times 8$ |

Variable light chain, variable heavy chain and single chain Fv (scFv) DNA fragments were generated by gene synthesis. Human Gamma-1 heavy chain and human kappa light chain DNA fragments were generated by gene synthesis. The fragments were assembled together by DNA ligation using restriction sites and cloned into a vector that is designed for transient expression in mammalian cells. The vector contains a strong CMV-derived promoter, and other upstream and downstream elements required for transient expression. The resulting IgG expression plasmids were verified as containing the expected DNA sequences by DNA sequencing. Transient expression of the antibody constructs was achieved using transfection of suspension-adapted HEK293F cells with linear PEI as described in CSH Protocols; 2008; doi:10.1101/pdb.prot4977. Briefly, add DNA to each tube containing F17 expression medium that has been pre-warmed at 37° C. followed by PEI. Incubate for 15 minutes at room temperature and add the DNA/PEI mixture to the flask containing HEK293 cells at a density of around $1\times10^6$ cells/ml in F17 Complete Medium. Incubate for 5 days at 37° C. with shaking after which the sample was centrifuged and the supernatant was collected and stored at 4° C. for purification.

Antibodies were purified from the resulting transfection supernatants using protein an affinity chromatography and Size Exclusion Chromatography when needed. Protein quality is analysed by Superdex 200 column. Protein used for all the assays have a purity of greater than 90%.

The bispecific antibodies specific to two different epitopes of HER2 can be used for the treatment of many HER2 expressed cancers such as breast, ovary, stomach, esophageal, prostate, lung and neuroendocrine cancers.

In one embodiment, the bispecific antibody is of tetravalent dual specificity. It includes an IgG and two scFv, which provides two different binding specificities compared to mono-specific antibody IgG. The IgG component provides stability over other bispecific antibodies used only scFv such as BiTE technology (Lutterbuese et al, *Proceedings of the National Academy of Sciences of the United States of America* 107.28 (2010): 12605-12610. PMC. Web. 2 Dec. 2014) and others (U.S. Pat. No. 7,332,585). It is also capable of mediating ADCC while those without Fc component cannot (U.S. Pat. No. 7,332,585). The tetravalent dual specificity nature provides the bispecific antibody a simultaneous binding capability over some other bispecific antibodies, which may only bind one antigen at a time (Kontermann, *MAbs.* 2012 March-April; 4(2):182-97; Schanzer et al, *Antimicrob. Agents Chemother.* 2011, 55(5):2369; EP272942).

For the convenience of narration, the sequences of or related to the bispecific antibodies are summarized in TABLE 2 herein-below.

TABLE 2

Summary of nucleotide and amino acid sequences of or related to the bispecific antibodies

| | |
|---|---|
| SI-4C1 SEQUENCES | |
| SEQ ID NO 1 | SI-4C1 Light Chain full-length nucleotide sequence |
| SEQ ID NO 2 | SI-4C1 Light Chain variable light chain nucleotide sequence |
| SEQ ID NO 3 | si-4c1 light chain full-length amino acid sequence. human kappa constant domain is underlined |
| SEQ ID NO 4 | si-4c1 light chain variable light chain amino acid sequence. complementarity determining regions are underlined |
| SEQ ID NO 5 | si-4c1 heavy chain full-length nucleotide sequence |
| SEQ ID NO 6 | SI-4C1 heavy Chain variable heavy chain nucleotide sequence |
| SEQ ID NO 7 | si-4c1 heavy chain full-length amino acid sequence. human gamma-1 domain is underlined |
| SEQ ID NO 8 | si-4c1 heavy chain variable heavy chain amino acid sequence. complementarity determining regions are underlined |
| SI-4C2 SEQUENCES | |
| SEQ ID NO 9 | SI4C2 Light Chain full-length nucleotide sequence |
| SEQ ID NO 10 | SI-4C2 Light Chain variable light chain nucleotide sequence |
| SEQ ID NO 11 | si-4c2 light chain full-length amino acid sequence. human kappa constant domain is underlined |
| SEQ ID NO 12 | si-4c2 light chain variable light chain amino acid sequence. complementarity determining regions are underlined |
| SEQ ID NO 13 | si-4c2 heavy chain full-length nucleotide sequence |
| SEQ ID NO 14 | SI-4C2 heavy Chain variable heavy chain nucleotide sequence |
| SEQ ID NO 15 | si-4c2 heavy chain full-length amino acid sequence. human gamma-1 domain is underlined |
| SEQ ID NO 16 | si-4c2 heavy chain variable heavy chain amino acid sequence. complementarity determining regions are underlined |
| SI-4C3 SEQUENCES | |
| SEQ ID NO 17 | SI-4C3 full-length nucleotide sequence |
| SEQ ID NO 18 | SI-4C3 FULL-LENGTH PROTEIN SEQUENCE. human gamma-1 domain is underlined, connector is in italics, scfv is in bold |
| SEQ ID NO 19 | SI-4C3 scfv amino acid sequence. order: vh-linker-vl. complementarity determining regions are underlined. linker is in bold italice |

TABLE 2-continued

| Summary of nucleotide and amino acid sequences of or related to the bispecific antibodies | |
|---|---|
| SI-4C4 SEQUENCES | |
| SEQ ID NO 20 | SI-4C4 full-length nucleotide sequence |
| SEQ ID NO 21 | SI-4C4 FULL-LENGTH PROTEIN SEQUENCE. human gamma-1 domain is underlined, connector is in italics, scfv is in bold |
| SEQ ID NO 22 | SI-4C4 scfv amino acid sequence. order: vh-linker-vl. complementarity determining regions are underlined. linker is in bold italice |
| Si-4X1 sequences | |
| SEQ ID NO 23 | SI4X1 Light Chain full-length nucleotide sequence |
| SEQ ID NO 24 | SI-4X1 Light Chain variable light chain nucleotide sequence |
| SEQ ID NO 25 | si-4X1 light chain full-length amino acid sequence. human kappa constant domain is underlined |
| SEQ ID NO 26 | si-4X1 light chain variable light chain amino acid sequence. complementarity determining regions are underlined |
| SEQ ID NO 27 | si-4X1 Bispecific heavy chain full-length nucleotide sequence |
| SEQ ID NO 28 | SI-4X1 bispecific heavy Chain variable heavy chain nucleotide sequence |
| SEQ ID NO 29 | SI-4X1 bispecific heavy chain scfv nucleotide sequence |
| SEQ ID NO 30 | si-4x1 bispecific heavy chain full-length amino acid sequence. human gamma-1 domain is underlined, connector is in italics, scfv is in bold |
| SEQ ID NO 31 | si-4x1 bispecific heavy chain variable heavy chain amino acid sequence. complementarity determining regions are underlined |
| SEQ ID NO 32 | si4x1 bispecific heavy chain scfv amino acid sequence. order: vh-linker-vl. complementarity determining regions are underlined. linker is in bold italics |
| Si-4X2 sequences | |
| SEQ ID NO 33 | SI4X2 Light Chain full-length nucleotide sequence |
| SEQ ID NO 34 | SI-4X2 Light Chain variable light chain nucleotide sequence |
| SEQ ID NO 35 | si-4X2 light chain full-length amino acid sequence. human kappa constant domain is underlined |
| SEQ ID NO 36 | si-4X2 light chain variable light chain amino acid sequence. complementarity determining regions are underlined |
| SEQ ID NO 37 | si-4X2 Bispecific heavy chain full-length nucleotide sequence |
| SEQ ID NO 38 | SI-4X2 bispecific heavy Chain variable heavy chain nucleotide sequence |
| SEQ ID NO 39 | SI-4X2 bispecific heavy chain scfv nucleotide sequence |
| SEQ ID NO 40 | si-4x2 bispecific heavy chain full-length amino acid sequence. human gamma-1 domain is underlined, connector is in italics, scfv is in bold |
| SEQ ID NO 41 | si-4x2 bispecific heavy chain variable heavy chain amino acid sequence. complementarity determining regions are underlined |
| SEQ ID NO 42 | si4x2 bispecific heavy chain scfv amino acid sequence. order: vh-linker-vl. complementarity determining regions are underlined. linker is in bold italics |
| Si-4X3 sequences | |
| SEQ ID NO 43 | SI4X3 Light Chain full-length nucleotide sequence |
| SEQ ID NO 44 | SI-4X3 Light Chain variable light chain nucleotide sequence |
| SEQ ID NO 45 | si-4X3 light chain full-length amino acid sequence. human kappa constant domain is underlined |
| SEQ ID NO 46 | si-4X3 light chain variable light chain amino acid sequence. complementarity determining regions are underlined |
| SEQ ID NO 47 | si-4X3 Bispecific heavy chain full-length nucleotide sequence |
| SEQ ID NO 48 | SI-4X3 bispecific heavy Chain variable heavy chain nucleotide sequence |
| SEQ ID NO 49 | SI-4X3 bispecific heavy chain scfv nucleotide sequence |
| SEQ ID NO 50 | si-4x3 bispecific heavy chain full-length amino acid sequence. human gamma-1 domain is underlined, connector is in italics, scfv is in bold |
| SEQ ID NO 79 | si-4x3 bispecific heavy chain variable heavy chain amino acid sequence. complementarity determining regions are underline |

TABLE 2-continued

| Summary of nucleotide and amino acid sequences of or related to the bispecific antibodies | |
|---|---|
| SEQ ID NO 80 | si4x3 bispecific heavy chain scfv amino acid sequence. order: vh-linker-vl. complementarity determining regions are underlined, linker is in bold italics |
| Si-4X4 sequences | |
| SEQ ID NO 51 | SI4X4 Light Chain full-length nucleotide sequence |
| SEQ ID NO 52 | SI-4X4 Light Chain variable light chain nucleotide sequence |
| SEQ ID NO 53 | si-4X4 light chain full-length amino acid sequence. human kappa constant domain is underlined |
| SEQ ID NO 54 | si-4X4 light chain variable light chain amino acid sequence. complementarity determining regions are underlined |
| SEQ ID NO 55 | si-4X4 Bispecific heavy chain full-length nucleotide sequence |
| SEQ ID NO 56 | SI-4X4 bispecific heavy Chain variable heavy chain nucleotide sequence |
| SEQ ID NO 57 | SI-4X4 bispecific heavy chain scfv nucleotide sequence |
| SEQ ID NO 58 | si-4x4 bispecific heavy chain full-length amino acid sequence. human gamma-1 domain is underlined, connector is in italics, scfv is in bold |
| SEQ ID NO 59 | si-4x4 bispecific heavy chain variable heavy chain amino acid sequence. complementarity determining regions are underlined |
| SEQ ID NO 60 | si4x4 bispecific heavy chain scfv amino acid sequence. order: vh-linker-vl. complementarity determining regions are underlined, linker is in bold italics |
| SI-4C5 SEQUENCES | |
| SEQ ID NO 61 | SI-4C5 full-length nucleotide sequence |
| SEQ ID NO 62 | SI-4C5 FULL-LENGTH PROTEIN SEQUENCE. human gamma-1 domain is underlined, connector is in italics, scfv is in bold |
| SEQ ID NO 63 | SI-4C5 scfv amino acid sequence. order: vh-linker-vl. complementarity determining regions are underlined. linker is in bold italice |
| SI-4C6 SEQUENCES | |
| SEQ ID NO 64 | SI-4C6 full-length nucleotide sequence |
| SEQ ID NO 65 | SI-4C6 FULL-LENGTH PROTEIN SEQUENCE. human gamma-1 domain is underlined, connector is in italics, scfv is in bold |
| SEQ ID NO 66 | SI-4C6 scfv amino acid sequence. order: vh-linker-vl. complementarity determining regions are underlined. linker is in bold italice |
| SI-4C7 SEQUENCES | |
| SEQ ID NO 67 | SI-4C7 full-length nucleotide sequence |
| SEQ ID NO 68 | SI-4C7 FULL-LENGTH PROTEIN SEQUENCE. human gamma-1 domain is underlined, connector is in italics, scfv is in bold |
| SEQ ID NO 69 | SI-4C7 scfv amino acid sequence. order: vh-linker-vl. complementarity determining regions are underlined. linker is in bold italice |
| SI-4C8 SEQUENCES | |
| SEQ ID NO 70 | SI-4C8 full-length nucleotide sequence |
| SEQ ID NO 71 | SI-4C8 FULL-LENGTH PROTEIN SEQUENCE. human gamma-1 domain is underlined, connector is in italics, scfv is in bold |
| SEQ ID NO 72 | SI-4C8 scfv amino acid sequence. order: vh-linker-vl. complementarity determining regions are underlined. linker is in bold italice |
| SI-4C10 SEQUENCES | |
| SEQ ID NO 73 | SI-4C10 full-length nucleotide sequence |
| SEQ ID NO 74 | SI-4C10 FULL-LENGTH PROTEIN SEQUENCE. human gamma-1 domain is underlined, connector is in italics, scfv is in bold |
| SEQ ID NO 75 | SI-4C10 scfv amino acid sequence. order: vh-linker-vl. complementarity determining regions are underlined. linker is in bold italice |
| SI-4C11 SEQUENCES | |
| SEQ ID NO 76 | SI-4C11 full-length nucleotide sequence |
| SEQ ID NO 77 | SI-4C11 FULL-LENGTH PROTEIN SEQUENCE. human gamma-1 domain is underlined, connector is in italics, scfv is in bold |

TABLE 2-continued

| Summary of nucleotide and amino acid sequences of or related to the bispecific antibodies | |
|---|---|
| SEQ ID NO 78 | SI-4C11 scfv amino acid sequence. order: vh-linker-vl. complementarity determining regions are underlined. linker is in bold italice |
| SEQ ID NO 81 | linkers |

EXAMPLES

Example 1

To assess the growth inhibitory potential of anti-HER2 antibodies, the effect on proliferation of BT-474 cells (ATCC HTB-20, Manassas, Va.) which are a mammary ductal carcinoma tumor line was tested. Cells were seeded into 96-well tissue culture plates at a density of 6000 cells/well in 100 μl RPMI-1640 medium containing 1% fetal bovine serum. After 4 hours, test antibodies were added at various concentrations, ranging from 0.0061 nM to 400 nM. Cells were cultured in the presence of test antibodies for 7 days. To each well, 20 μl of MTS reagent (Promega, Madison, Wis.) was added and cells were incubated at 37° C. for 2 hours. MTS is readily taken up by actively proliferating cells, reduced into formazan (which readily absorbs light at 490 nm), and then secreted into the culture medium. Following incubation, OD490 values were measured using a BioTek (Winooski, Vt.) ELx800 absorbance reader. OD490 values for control cells (treated with medium only) were also obtained in this manner at the time of antibody addition in order to establish baseline metabolic activity. Proliferation may be calculated by subtracting the control baseline OD490 from the 72 hour OD490. Data from antibody titrations was expressed at % of control population according to the following formula: % of control proliferation=(test proliferation/control proliferation)*100.

Figure 5:
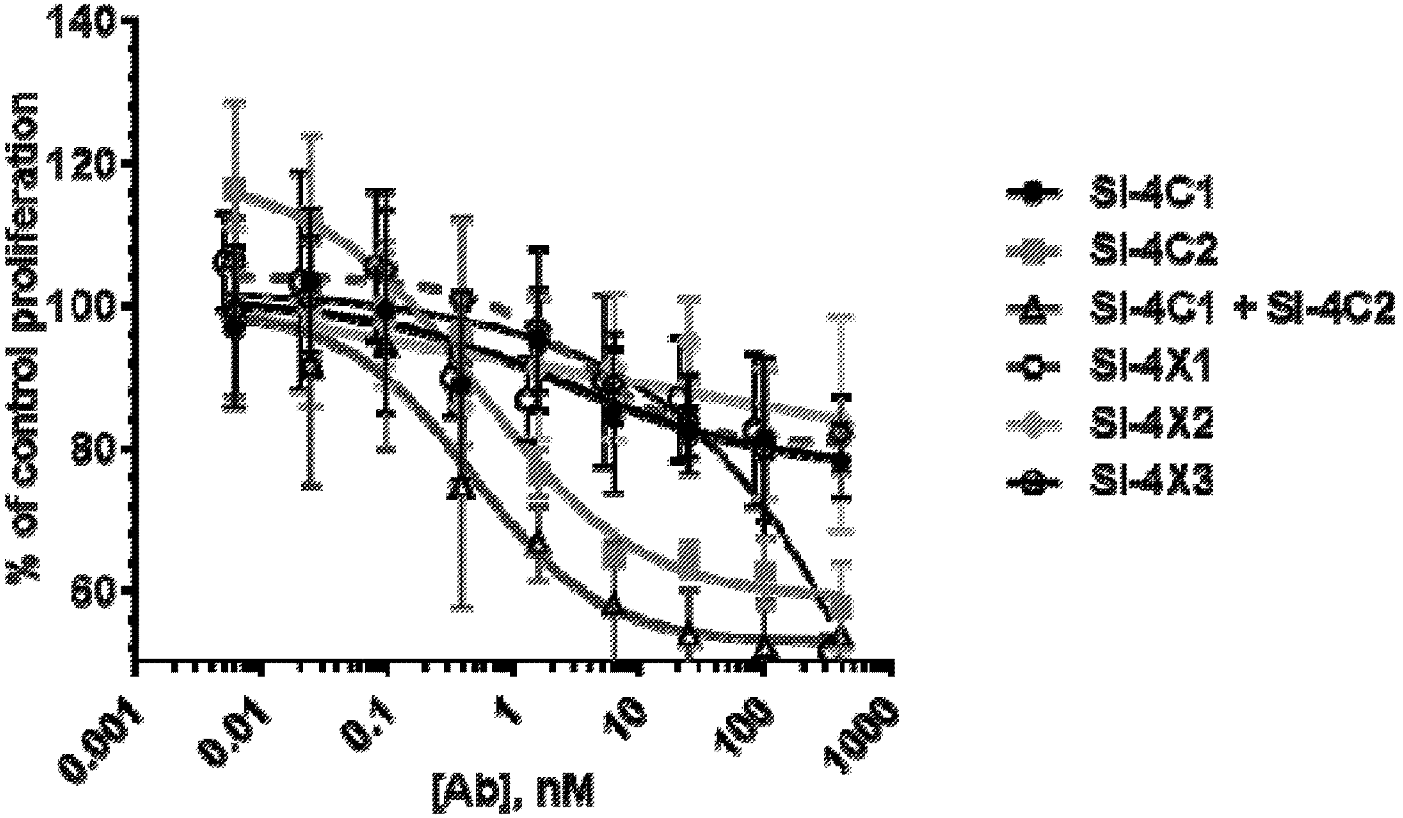
FIG. 5 shows effect of SI-4X and SI-4C antibodies on BT-474 cell proliferation.
Figure 6:
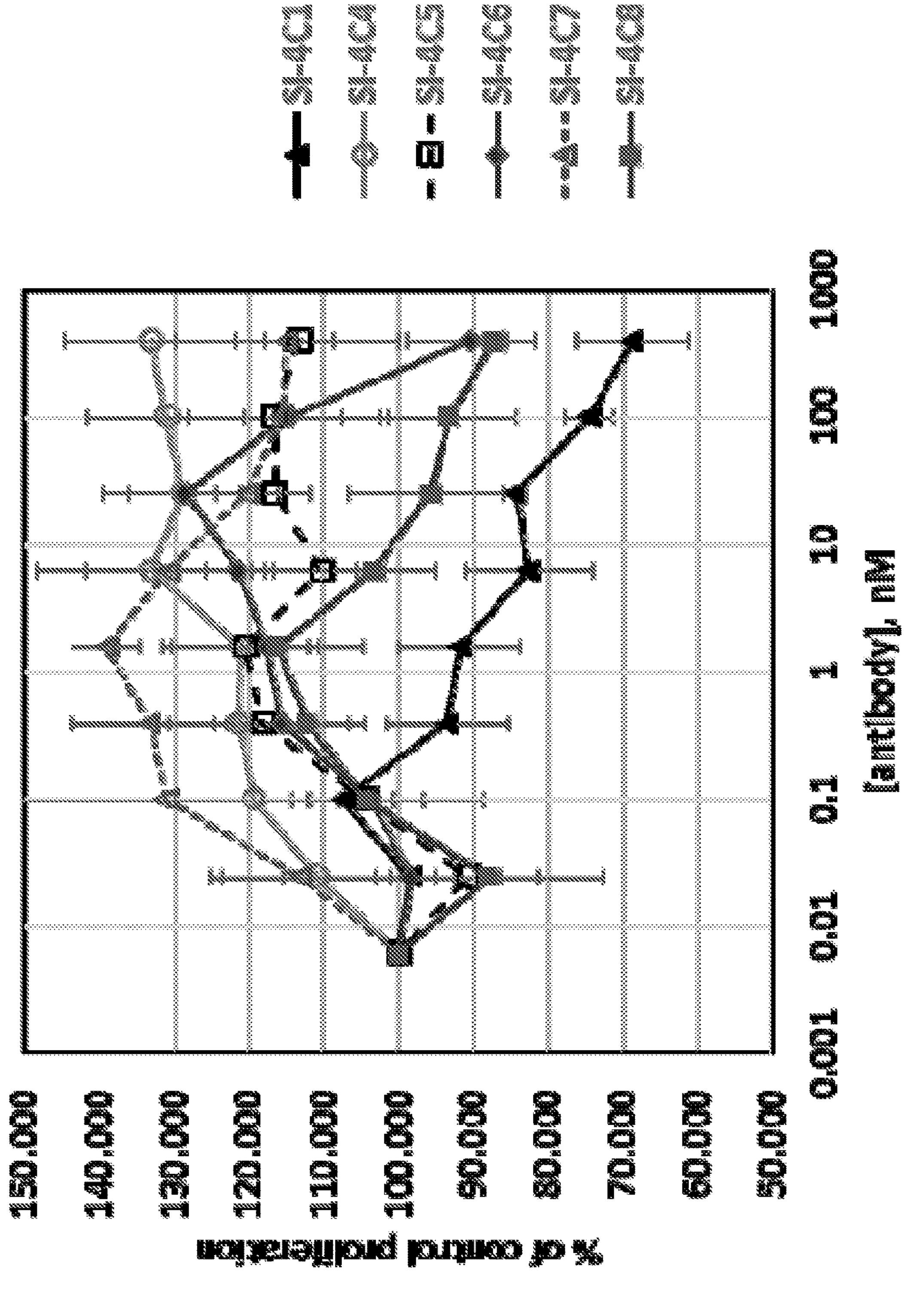
FIG. 6 shows effect of extending connector length from 10 amino acids to 30 amino acids on BT-474 cell proliferation.
Figure 7:
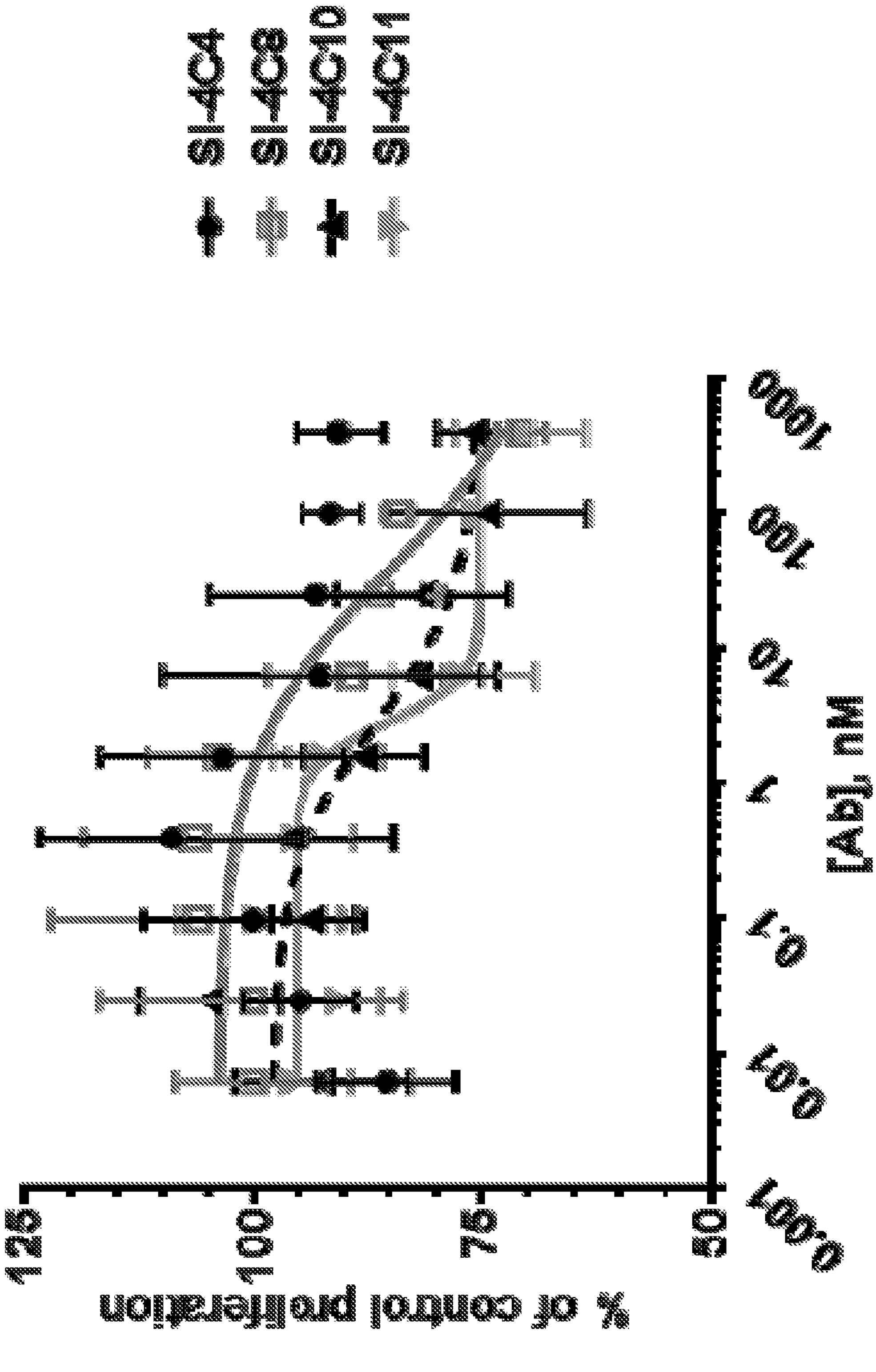
FIG. 7 shows effect of extending connector length up to 40 amino acids on BT-474 cell proliferation

The effect of SI-4X1 and SI-4X2 on BT-474 proliferation is shown in FIG. 5. Both molecules had anti-proliferative effect, but neither was as efficacious as the control antibody SI-4C2 or the combination of the control antibodies SI-4C1 and SI-4C2. Increasing the length of the connector $G_4S$ linker which separates the C-terminal scFv from huIgG from 2 repeats to 6 repeats increased the efficacy, as can be seen from SI-4X3. It is suspected that the lower efficacy of the bispecific antibodies could be the result of pro-proliferative activity supplied by the C-terminal scFv. There is precedence in the literature for anti-Her2 antibodies showing agonistic activity depending on their structure. To investigate this, we create a series of control molecules containing the same anti-Her2 scFv, but with progressively longer $G_4S$ linkers. As can be seen in FIG. 6, anti-proliferative effect was directly proportional to the number of $G_4S$ elements in the linker, with SI-4C8 (6 repeats) showing the highest degree of anti-proliferative activity, while SI-4C4 (2 repeats) exhibited agonistic activity. This effect is even more pronounced when the linker is increased to 7 (SI-4C10) and 8 (SI-4C11) repeats and can be seen in FIG. 7.

Example 2

The ability of anti-Her2 antibodies to be internalized by BT-474 cells was tested. One milligram aliquots of antibody in standard PBS were allowed to react with Alexa Fluor 488 carboxylic acid, TFP ester (Thermo Fisher # A-10235, Waltham, Mass.) for one hour at room temperature. Unincorporated dye was removed by gel filtration using a Bio-Gel P-30 column. Following conjugation, aliquots of $3\times10^5$ BT-474 cells were incubated with 50 nM each Alexa 488 labeled antibody in complete medium (RPMI-1640+10% FBS) for 1 hour at either 37° C. or 4° C. (ice). Following incubation, cells were washed twice in a cold centrifuge with ice cold PBS. Cells were then resuspended in either 500 nM quenching rabbit-anti-Alexa488 antibody (Thermo Fisher # A-11094, Waltham, Mass.) or 500 nM rabbit IgG isotype control antibody (Jackson ImmunoResearch Laboratories #011-000-003, West Grove, Pa.) and incubated on ice for 30 minutes. Two volumes of 2% paraformaldehyde were added to each sample and incubated for 10 minutes at room temperature. Cells were then washed once with 1 ml ice cold PBS, resuspended in 200 μl PBS and analyzed using a FACScalibur flow cytometer. Geometric mean fluorescence (GMFI) from $2\times10^4$ events per sample was used to calculate the percentage of internalized antibody. Since no internalization should occur at 4° C., the fluorescence measured in samples incubated on ice followed by incubation with the anti-Alexa488 antibody was considered to be unquenchable background surface fluorescence and was subtracted from GMFI values obtained samples incubated at 37° C. prior to quenching. Internalization was calculated as follows: % internalization=(GMFI quenched/GMFI unquenched)*100.

Figure 8:
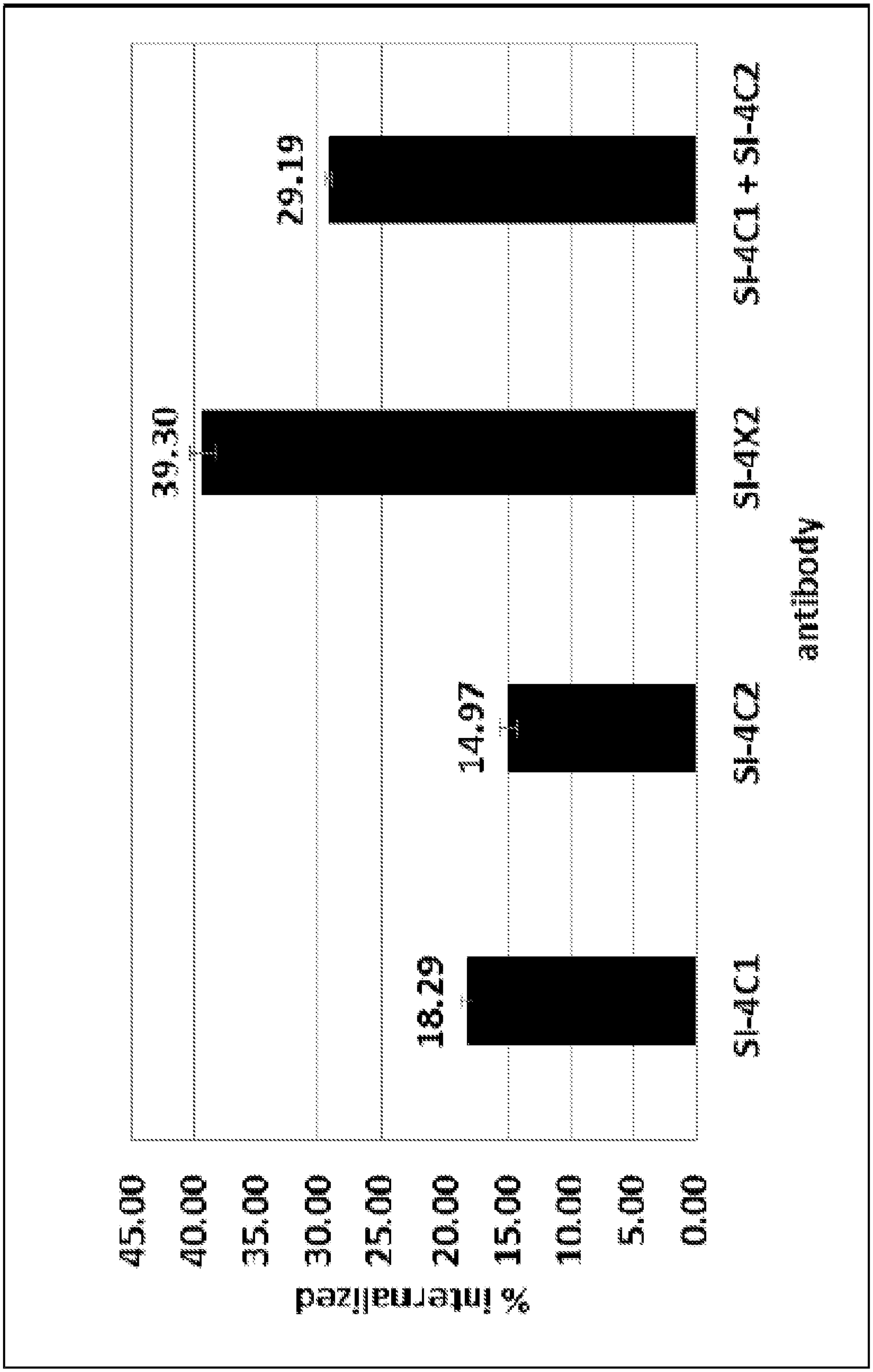
FIG. 8 shows effect of SI-4X antibodies on HER2 internalization on BT-474 cell.

The results may be seen in FIG. 8. The bispecific antibody, SI-4X2 internalized to a greater degree (39.3%) than the monospecific control antibodies SI-4C1 (18.29%) and SI-4C2 (14.97%) as well as the combination of 51-4C1+SI-4C2 (29.19%).

Pharmaceutical Compositions

The term "effective amount" refers to an amount of a drug effective to achieve a desired effect, e.g., to ameliorate disease in a subject. Where the disease is a caner, the effective amount of the drug may inhibit (for example, slow to some extent, inhibit or stop) one or more of the following example characteristics including, without limitation, cancer cell growth, cancer cell proliferation, cancer cell motility, cancer cell infiltration into peripheral organs, tumor metastasis, and tumor growth. Wherein the disease is a caner, the effective amount of the drug may alternatively do one or more of the following when administered to a subject: slow or stop tumor growth, reduce tumor size (for example, volume or mass), relieve to some extent one or more of the symptoms associated with the cancer, extend progression free survival, result in an objective response (including, for example, a partial response or a complete response), and increase ovral survival time. To the extent the drug may prevent growth and/or kill existing cancer cells, it is cytostatic and/or cytotoxic.

With respect to the formulation of suitable compositions for administration to a subject such as a human patient in need of treatment, the antibodies disclosed herein may be mixed or combined with pharmaceutically acceptable carriers known in the art dependent upon the chosen route of administration. There are no particular limitations to the modes of application of the antibodies disclosed herein, and the choice of suitable administration routes and suitable compositions are known in the art without undue experimentation.

Although many forms of administration are possible, an example administration form would be a solution for injection, in particular for intravenous or intra-arterial injection. Usually, a suitable pharmaceutical composition for injection may include pharmaceutically suitable carriers or excipients such as, without limitation, a buffer, a surfactant, or a stabilizer agent. Example buffers may include, without limitation, acetate, phosphate or citrate buffer. Example surfactants may include, without limitation, polysorbate. Example stabilizer may include, without limitation, human albumin.

Similarly, persons skilled in the art have the ability to determine the effective amount or concentration of the antibodies disclosed therein to effective treat a condition such as a cancer. Other parameters such as the proportions of the various components in the pharmaceutical composition, administration does and frequency may be obtained by a person skilled in the art without undue experimentation. For example, a suitable solution for injection may contain, without limitation, from about 1 to about 20, from about 1 to about 10 mg antibodies per ml. The example dose may be, without limitation, from about 0.1 to about 20, from about 1 to about 5 mg/Kg body weight. The example administration frequency could be, without limitation, once per day or three times per week.

While the present disclosure has been described with reference to particular embodiments or examples, it may be understood that the embodiments are illustrative and that the disclosure scope is not so limited. Alternative embodiments of the present disclosure may become apparent to those having ordinary skill in the art to which the present disclosure pertains. Such alternate embodiments are considered to be encompassed within the scope of the present disclosure. Accordingly, the scope of the present disclosure is defined by the appended claims and is supported by the foregoing description.

What is claimed is:

1. A bispecific tetravalent antibody, said bispecific tetravalent antibody comprising:

two IgG1 heavy chains;

two kappa light chains; and two single chain Fv (scFv) domains;

wherein the two IgG1 heavy chains and kappa light chains form an IgG moiety with a binding specificity to a first domain of HER2;

wherein the two scFv domains have a binding specificity to a second domain of HER2, and each scFv domain is connected to the C-terminal residue of either of the IgG1 heavy chains by a connector having an amino acid sequence of (gly-gly-gly-gly-ser)$_n$ ($(G_4S)_n$); wherein n is an integral of at least 2;

wherein each scFv domain has a structure order of N terminus-variable heavy domain-linker-variable light domain-C terminus or N-terminus-variable light domain-linker-variable heavy domain-C terminus, and wherein the linker is comprised of amino acid sequence of (gly-gly-gly-gly-ser)$_m$ ($(G_4S)_m$); wherein m is an integral of at least 3, and wherein at least one of the IgG1 heavy chains comprises the amino acid sequence of SEQ ID NO 40.

2. An isolated nucleic acid encoding the antibody of claim 1.

3. An expression vector comprising the isolated nucleic acid of claim 2.

4. A host cell comprising the nucleic acid of claim 2.

5. A host cell comprising the expression vector of claim 3.

6. A pharmaceutical composition, comprising the bispecific tetravalent antibody of claim 1 and a pharmaceutically acceptable carrier.

7. The bispecific tetravalent antibody of claim 1, wherein m is 3, 4, 5 or 6.

8. The bispecific tetravalent antibody of claim 1, wherein at least one of the IgG1 heavy chains is a humanized or human IgG1 heavy chain.

9. The bispecific tetravalent antibody of claim 1, wherein at least one of the kappa light chains is a humanized or human kappa light chain.

10. The bispecific tetravalent antibody of claim 1, wherein both kappa light chains are humanized or human kappa light chains.

11. The bispecific tetravalent antibody of claim 1, wherein the first or the second domain of HER2 is independently selected from domain 2 and domain 4 of HER2.

12. The bispecific tetravalent antibody of claim 1, wherein the IgG moiety has a binding specificity for domain 2 of HER2.

13. The bispecific tetravalent antibody of claim 1, wherein the scFv domains have a binding specificity for domain 4 of HER2.

14. The bispecific tetravalent antibody of claim 1, wherein the IgG moiety has a binding specificity for domain 2 of HER2, and the scFv domains have a binding specificity for domain 4 of HER2 simultaneously.

15. The bispecific tetravalent antibody of claim 1, wherein the IgG moiety has a binding specificity for domain 4 of HER2, and the scFv domains have a binding specificity for domain 2 of HER2 simultaneously.

16. The bispecific tetravalent antibody of claim 1, wherein at least one of the kappa light chains comprises an amino acid sequence selected from SEQ ID NO 3, 11, 25, 35, 45, and 53.

17. The bispecific tetravalent antibody of claim 1, wherein at least one of variable light chain comprises an amino acid sequence selected from SEQ ID NO 4, 12, 26, 36, 46, and 54.

18. The bispecific tetravalent antibody of claim 1, wherein the antibody binds to domain 4 of HER2 with a Kd less than 30 nM and binds to domain 2 of HER2 with a Kd less than 30 nM.

* * * * *